(12) United States Patent
Narula

(10) Patent No.: US 12,174,168 B2
(45) Date of Patent: Dec. 24, 2024

(54) APPARATUS FOR MICROBIAL ACTIVITY DETECTION AND INVENTORY MANAGEMENT, AND PROCESS THEREOF

(71) Applicant: Poonam Narula, Sunnyvale, CA (US)

(72) Inventor: Poonam Narula, Sunnyvale, CA (US)

( * ) Notice: Subject to any disclaimer, the term of this patent is extended or adjusted under 35 U.S.C. 154(b) by 867 days.

(21) Appl. No.: 17/288,296

(22) PCT Filed: Oct. 25, 2019

(86) PCT No.: PCT/US2019/058220
§ 371 (c)(1),
(2) Date: Apr. 23, 2021

(87) PCT Pub. No.: WO2020/087043
PCT Pub. Date: Apr. 30, 2020

(65) Prior Publication Data
US 2021/0382026 A1 Dec. 9, 2021

Related U.S. Application Data

(60) Provisional application No. 62/750,451, filed on Oct. 25, 2018.

(51) Int. Cl.
*G01N 33/02* (2006.01)
*C12Q 1/04* (2006.01)
(Continued)

(52) U.S. Cl.
CPC ............... *G01N 33/02* (2013.01); *C12Q 1/04* (2013.01); *G01N 21/03* (2013.01); *G01N 21/51* (2013.01);
(Continued)

(58) Field of Classification Search
CPC ........ G01N 33/02; G01N 21/03; G01N 21/51; G01N 21/61; G01N 21/783; G01N 21/82;
(Continued)

(56) References Cited

U.S. PATENT DOCUMENTS

| 4,003,709 A | 1/1977 | Eaton et al. | |
| 4,659,550 A * | 4/1987 | Schildknecht | G01N 33/4905 422/534 |

(Continued)

FOREIGN PATENT DOCUMENTS

| CN | 207115219 U | 3/2018 |
| EP | 3168608 A1 | 5/2017 |

(Continued)

OTHER PUBLICATIONS

Sousa, A.R. et al.; "Determination of the respiration rate parameters of cherry tomatoes and their joint confidence regions using closed systems," Journal of Food Engineering, 2017, pp. 12-22, vol. 206.

(Continued)

*Primary Examiner* — Michael L Hobbs
(74) *Attorney, Agent, or Firm* — Casimir Jones, SC; Tristan A. Fuierer

(57) ABSTRACT

A system and method for the real time determination of microbial growth in or on perishable products. The system can predict the extent of microbial growth, e.g., whether food is spoiled, in real time by measuring chemicals released, e.g., $CO_2$, from the perishable product during microbial growth. The output from a sensor can be correlated to the extent of microbial growth, i.e., spoilage, and provide information about the extent of microbial growth to the user, for example, through their smart devices.

20 Claims, 13 Drawing Sheets

(51) Int. Cl.
*G01N 21/03* (2006.01)
*G01N 21/51* (2006.01)
*G01N 21/61* (2006.01)
*G01N 21/78* (2006.01)
*G01N 21/82* (2006.01)

(52) U.S. Cl.
CPC .......... *G01N 21/61* (2013.01); *G01N 21/783* (2013.01); *G01N 21/82* (2013.01); *G01N 2021/513* (2013.01); *G01N 2201/1211* (2013.01)

(58) Field of Classification Search
CPC ............ G01N 21/01; G01N 2021/513; G01N 2201/1211; G01N 2201/0245; G01N 2201/064; G01N 2201/1214; C12Q 1/04
See application file for complete search history.

(56) References Cited

U.S. PATENT DOCUMENTS

| | | | |
|---|---|---|---|
| 6,453,687 B2 | 9/2002 | Sharood et al. | |
| 7,372,003 B2 | 5/2008 | Kates | |
| 8,449,834 B2 | 5/2013 | Ostrowski et al. | |
| 8,933,210 B2 | 1/2015 | Lu et al. | |
| 9,989,474 B2 | 6/2018 | Song et al. | |
| 10,157,340 B2 | 12/2018 | Swager et al. | |
| 10,185,733 B2 | 1/2019 | Knobel | |
| 10,203,678 B2 | 2/2019 | Lagares-Greenblatt et al. | |
| 10,215,644 B2 | 2/2019 | Lawler, Jr. | |
| 10,247,713 B2 | 4/2019 | Smyth et al. | |
| 10,267,667 B2 | 4/2019 | Gurumohan et al. | |
| 10,286,368 B2 | 5/2019 | Deshpande | |
| 10,289,612 B2 | 5/2019 | Knobel | |
| 10,320,582 B1 | 6/2019 | Wallace et al. | |
| 10,323,982 B2 | 6/2019 | Goldring et al. | |
| 10,324,042 B2 | 6/2019 | Heacock | |
| 10,324,439 B2 | 6/2019 | Lagares-Greenblatt et al. | |
| 10,326,537 B2 | 6/2019 | Johansen | |
| 10,332,421 B2 | 6/2019 | Minvielle | |
| 10,338,048 B2 | 7/2019 | La Valle Sansone et al. | |
| 2004/0077075 A1 | 4/2004 | Jensen et al. | |
| 2005/0153052 A1 | 7/2005 | Williams et al. | |
| 2005/0254055 A1 | 11/2005 | Peng | |
| 2005/0266516 A1* | 12/2005 | Kanipayor | C12Q 1/04 435/287.1 |
| 2006/0096871 A1 | 5/2006 | Manoukian et al. | |
| 2007/0176773 A1 | 8/2007 | Smolander et al. | |
| 2007/0222973 A1* | 9/2007 | Hoshiko | G01N 35/00603 356/436 |
| 2007/0285238 A1 | 12/2007 | Batra | |
| 2008/0040272 A1 | 2/2008 | Eskin | |
| 2008/0176273 A1* | 7/2008 | Eden | C12M 41/36 435/287.1 |
| 2011/0104738 A1 | 5/2011 | Forsell | |
| 2013/0293894 A1 | 11/2013 | Salerno et al. | |
| 2017/0089935 A1 | 3/2017 | Eden et al. | |
| 2017/0241930 A1 | 8/2017 | Roberts | |
| 2021/0246643 A1* | 8/2021 | Sonovani | A61L 2/24 |

FOREIGN PATENT DOCUMENTS

| | | |
|---|---|---|
| WO | 2013096243 A1 | 6/2013 |
| WO | 2018116294 A1 | 6/2018 |

OTHER PUBLICATIONS

Fonseca, Susana C., et al.; "Modelling respiration rate of fresh fruits and vegetables for modified atmosphere packages: a review," Journal of Food Engineering, 2002, pp. 99-119, vol. 52.
International Search Report, PCT/US19/44901, dated Oct. 24, 2019.
International Search Report, PCT/US19/58220, dated Jan. 21, 2020.

* cited by examiner

APPARATUS FOR MICROBIAL ACTIVITY DETECTION AND INVENTORY MANAGEMENT, AND PROCESS THEREOF

CROSS-REFERENCE TO RELATED APPLICATIONS

This application is filed under the provisions of 35 U.S.C. § 371 and claims the priority of International Patent Application No. PCT/US2019/058220 filed on 25 Oct. 2019 entitled "APPARATUS FOR MICROBIAL ACTIVITY DETECTION AND INVENTORY MANAGEMENT, AND PROCESS THEREOF" in the name of Poonam NARULA, which claims priority to U.S. Provisional Patent Application No. 62/750,451, filed on 25 Oct. 2018, both of which are hereby incorporated by reference herein in their entirety.

STATEMENT OF PRIORITY

This application claims priority to U.S. Provisional Application No. 62/750,451 filed on Oct. 25, 2018, the contents of which are incorporated by reference herein for all purposes.

TECHNICAL FIELD

The present invention relates to a system and method for the real time determination of food spoilage or freshness status.

BACKGROUND

It is estimated that 40% of the food supply in the United States is wasted. This waste, according to the USDA, is estimated at 130 billion tons of food per year, at a cost of $160 billion per year. On Oct. 18, 2018, the USDA, EPA and FDA signed a joint agreement entitled *Winning on Reducing Food Waste Initiative*, which aims to reduce food waste in the US by 50% by 2030. According to the United Nations Food and Agriculture Organization, the world population will have an additional 2 billion people by 2050 and this population explosion will require an optimization of the resources so that food insecurity, malnutrition and the effects of greenhouse gas emissions and fresh water consumption associated with food waste are minimized.

The term "perishable" is used to refer to products that are subject to spoilage or decay. The companies that make and/or sell these products, and the consumers that use them, are presented with the continuing problem of identifying which products have exceeded their shelf-life, especially when the perishable products are starting to spoil or otherwise lose their effectiveness. Manufacturers of perishable goods date code their products so that, either through sale or consumption by the purchaser, the products will be limited to a reasonable, measurable shelf life. Some perishable products are visually inspected to predict spoilage. Disadvantageously, these methods result in a large amount of waste since they employ an empirical determination of spoilage status.

There exist many known indicators of freshness of food products that indicate whether a certain food product may be spoiled. One of the prime indicators of food spoilage is microbial growth. On the other hand, some bacteria do not cause spoilage, but are actually added to milk or cream after pasteurization to make "cultured" products such as certain hard cheese. In those cases, spoilage would be measured by looking for common pathogenic indicators such as salmonella or *E. coli* 0157. Even though the strictest standards of care may be observed in the preparation, packaging, sealing, and sterilization of foodstuffs and their containers, it is virtually impossible to insure completely against the occasional presence of bacteria.

While alternatives to strict production and shelf life controls have been explored, there has been surprisingly little visible progress with respect to other solutions for identifying food spoilage. One such alternative solution, as suggested by the present invention, would be a system and method for the real time determination of food spoilage or indicator of food freshness which would allow the user of the system to readily and quickly identify the condition of the food within the container (e.g., good or bad/spoiled). From an economic standpoint, a reliable and inexpensive detection system could well eliminate the need for shelf life controls, thus reducing or eliminating losses from the disposal of perfectly good food products.

Towards this end, a $CO_2$ detection-based system to monitor the freshness of a perishable products and method of using same is described herein to reduce food waste. The system can predict the status of food freshness in real time by measuring chemicals or biologics released during food spoilage. The output from the chemical sensor can be correlated to the extent of spoilage and provide information to the user, for example, through their smart devices. The information can allow a user to make informed decisions about food consumption based on the freshness indicator. This system and method can have economies of scale and can be utilized by everyone in the food supply value chain, e.g., farms, processors, distributors, and storage as well as in retail stores, food service operations, and households.

SUMMARY

In one aspect, a detection device is described, said detection device comprising:
- a cuvette holder, wherein the cuvette holder has a shape and size that accommodates a cuvette, wherein the cuvette comprises a sample under test;
- at least one light source configured to generate a light beam and to direct the light beam to the sample under test;
- at least one detector configured to receive light that is one of transmitted through the sample or scattered by the sample, and configured to generate an output representative of one of the transmitted or scattered light; and
- a computing device configured to receive the output from the at least one detector and to determine a characteristic of the sample based on the received output.

In another aspect, an integrated cuvette holder is described, wherein the cuvette holder has a shape and size that accommodates a cuvette, said integrated cuvette holder comprising: (a) a holder for at least one light source and a corresponding aperture to direct light emanating from each light source to an interior space of the cuvette holder;
  (b) a holder for at least one detector and a corresponding aperture for the passage of light from the interior space of the cuvette holder to each detector;
  (c) optionally a holder for a temperature sensor;
  (d) optionally a holder for a humidity detector;
  (e) optionally a holder for an agitator,
  (f) optionally a holder for a battery;
  wherein the integrated cuvette holder is an enclosure that minimizes light in the interior space while simultaneously reducing electrical noise in the interior space from the at least one detector.

In still another aspect, a detection system is described, said detection system comprising:
a detection device comprising:
a cuvette holder, wherein the cuvette holder has a shape and size that accommodates a cuvette, wherein the cuvette comprises a sample under test;
at least one light source configured to generate a light beam and to direct the light beam to the sample under test;
at least one detector configured to receive light that is one of transmitted through the sample or scattered by the sample, and configured to generate an output representative of one of the transmitted or scattered light;
a first computing device configured to receive the output from the at least one detector and to determine a characteristic of the sample based on the received output; and
a communication module configured to communicate the determined characteristic of the sample; and
a second computing device configured to receive the determined characteristic of the sample.

Other aspects, features and embodiments of the invention will be more fully apparent from the ensuing disclosure and appended claims.

BRIEF DESCRIPTION OF THE DRAWINGS

The several objects, features, and advantages of this invention will be understood by reading this description in conjunction with the drawings, in which.

DETAILED DESCRIPTION

Figure 1:
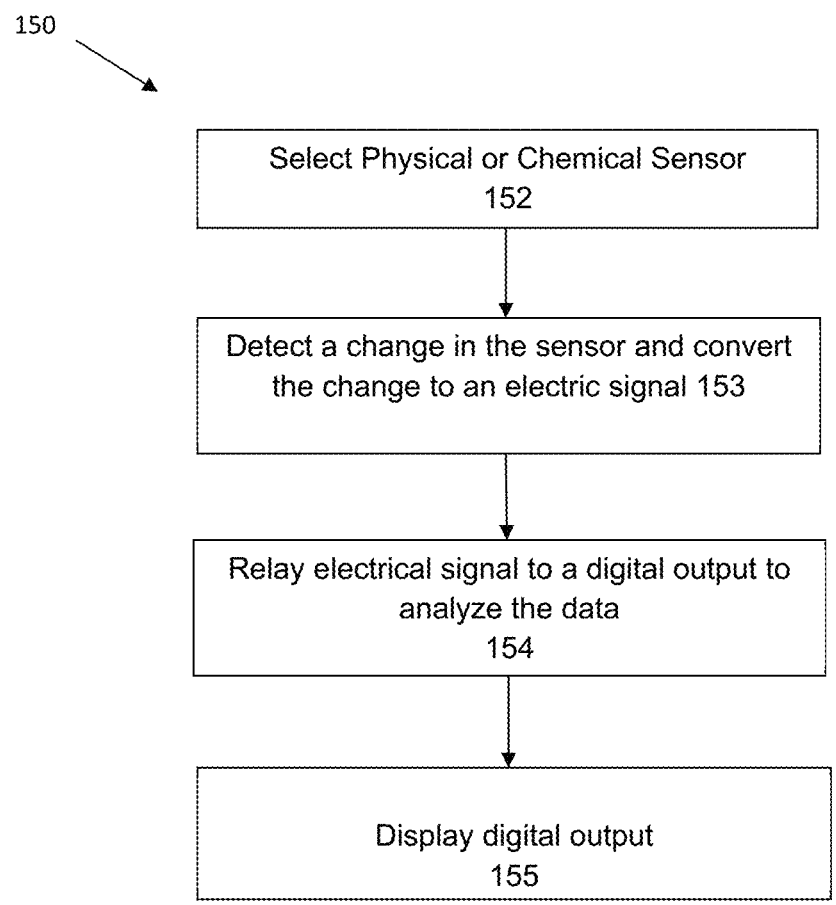
FIG. 1 is a flow chart of a generalized microbial growth detection system 150 described herein.

The present invention relates to a system and method for the real time determination of microbial growth in or on perishable products. The system can predict the extent of microbial growth, e.g., whether food is spoiled, in real time by measuring chemicals released, e.g., $CO_2$, during microbial growth. The output from the sensor can be correlated to the extent of microbial growth, i.e., spoilage, and provide information to the user, for example, through their smart devices.

Under normal packing conditions, when a food product within a sealed container or package starts to spoil, several byproducts are formed and they accumulate therein. It is theoretically possible to detect spoilage of perishable products by detecting one or more spoilage by-products. Common to all such deterioration is the production of heat, acidity, pressure, and carbon dioxide ($CO_2$). Under packing conditions, microbes thrive during storage of food products and result in the formation of many chemical species including, but not limited to, lactic acid and acetic acid by lactic acid bacteria. Carbon dioxide is also known to be produced during any kind of bacterial or mold growth on foods. Ideally, a spoilage detection system should be useable with as many different food products as possible, without requiring different detection systems for each different type of perishable item.

The prior art evidences that heat and pressure are not practical ways to detect food spoilage. Chemicals that change color when pH changes have been used to mark the presence or absence of bacterial growth. Commonly utilized pH indicators include phenol red, bromocresol blue, and neutral red. Markers, such as electrical impedance, electrical conductivity, and the amount of ATP (adenosine triphosphate), have been measured from microbes growing in a general medium with the addition of a chemical that is measured. Tests for the above-mentioned markers can be accurate but are not practical and/or are expensive and unable to identify food spoilage in real time.

It is possible to detect carbon dioxide gas, a by-product of bacteria, to indicate the extent of deterioration of a perishable product. Such a detection device would be usable with the widest possible variety of perishable products. Such a detection device would have to operate independently of the other properties of products, such as pH, salt content (corrosiveness), pressure and/or vacuum. Further, such a detection device must be approved for use in connection with consumables and is preferably inexpensive to produce and easy to use.

U.S. Pat. No. 4,003,709 to Eaton et al teaches providing a liquid impermeable pouch in which a liquid carbon dioxide detecting solution is entrapped. The solution provides a visually observable change when the concentration of carbon dioxide rises substantially above that which is the normal ambient concentration of $CO_2$ for our atmosphere. A suitable opening is formed in a container and the pouch is sealed into and over the opening so that the inert plastic material seals the opening and the microporous plastic portion is inside the container in gaseous communication with the food contents. If carbon dioxide gas is generated within the container, e.g., as a result of deterioration of the food, the $CO_2$ will pass through the microporous plastic and react with the calcium hydroxide to precipitate calcium carbonate. This causes the solution to change from clear to milky white, and this change is observable from outside the container by looking through the window. Disadvantageously, turbidity is practical only for consumers with trained eyes or when expensive and bulky spectrophotometers are used. Furthermore, just because the solution in the pouch of U.S. Pat. No. 4,003,709 became turbid does not necessarily mean that the product is spoiled, which could result in the disposal of perishable product that is still safe to consume or use.

As defined herein, "perishable" or "perishables" is used to refer to products that are subject to spoilage or decay on or in said products. Perishable products comprise anything that is capable of supporting microbial growth including, but are not limited to, chilled and minimally processed foods and beverages, fresh produce, precut produce, cooked food, uncooked food, dairy products (e.g., milk, cheese), grains, meat, poultry, oils, waxes, roots, nuts, seafood, pharmaceuticals, supplements, solutions, ayurvedic remedy, pharmaceuticals, blood, beauty and hygiene products, medical aids (e.g., bandages, etc.), and medical devices, each of which has its own unique shelf-life. It also includes wounds on living matter, such as human beings, animals or on plants. Wounds can include, for example cuts, scrapes, stings, or any other format that exposes the surface that must undergo a healing process. The perishable products can be stored in environments appropriate for maintaining the usefulness of said product. Furthermore, the perishable products can be anywhere in the value chain, e.g., from farm-to-fork for food products. It should be appreciated by the person skilled in the art that reference to a perishable product can indicate that only one product is present for testing, e.g., just strawberries in a refrigerator, or at least two or more perishable products are present for testing, e.g., strawberries and blueberries in a refrigerator.

As defined herein, a "sensor" includes a device or system that can detect chemical or physical changes associated with microbial growth or microbial decay, and include for example, the detection of at least one of carbon dioxide, oxygen, ethylene, hydrogen sulfide, ammonia, volatile and non-volatile amines, total volatile nitrogen, volatile acids and bases, non-volatile acids and bases, slime formation, *E. coli, Salmonella, Listeria monocytogenes*, and combination thereof. In one embodiment, the sensor is a chemical sensor detecting carbon dioxide. In another embodiment, the sensor comprises a chemical sensor detecting carbon dioxide and a sensor that measures oxygen concentration, wherein respiration quotient, or ratio of $CO_2/O_2$, is reported.

As used herein, "shelf life status" is calculated by measuring a parameter that is the characteristic of the detection system including, but not limited to, Nephelometric Turbidity Units (NTU), milkiness, turbidity, opalescence, redox potential change, light intensity change, and color change.

As defined herein, "biopharmaceuticals" include, but are not limited to, antibodies, proteins, peptides, nucleic acids, polysaccharides, and combinations thereof.

Cuvettes are well known in the spectrophotometric arts, but as used herein, a "cuvette" is meant to describe a container that holds the chemical sensor or chemical sensor species. It should be appreciated that the cuvette can be of any shape or size, as required for the system and the location that said system will be positioned. Cuvette shapes contemplated include, but are not limited to, circular cylinders, cubic squares, rectangular parallelepiped shapes, polygonal prisms (e.g., triangular prisms, pentagonal prisms, hexagonal prisms), hemispheric shapes, semi-ellipsoid shapes, and cylindrical discs. A cuvette holder is preferentially of a shape and size to accommodate the cuvette such that the cuvette can be easily inserted into, and removed from, the cuvette holder. In addition, the cuvette holder can be designed to accommodate attachments including, but not limited to, a light source and at least one detector.

As used herein, a "medical device" is an instrument, apparatus, material, or other article, whether used alone or in combination, including software necessary for its application, intended by the manufacturer to be used for human beings or other species for diagnosis, prevention, monitoring treatment, or alleviation of disease; diagnosis, monitoring, treatment, or alleviation of or compensation for an injury or handicap; investigation, replacement, or modification of the anatomy or of a physiologic process; or control of conception, and that does not achieve its primary intended action in or on the human body by pharmacologic, immunologic, or metabolic means but might be assisted in its function by such means. A medical device includes, without limitation, a surgical instrument, a respiratory therapy instrument, an anesthesia instrument, a catheter, an implant, a probe, an endoscope, an arthroscope, a laparoscope, a blade, a cystoscope, a spirometer, a CPAP mask and tubing, dialysis instrument and accessories, a heart-lung machine and accessories, a heart-lung bypass machine and accessories, and a diaphragm fitting ring. Non-limiting examples of a probe includes an ultrasound probe and an esophageal manometry probe. Non-limiting examples of a catheter includes a cardiac catheter, a urinary catheter, an anorectal manometry catheter. Non-limiting examples of an endoscope includes a gastrointestinal endoscope, a bronchoscope, and a nasopharyngoscope. Non-limiting examples of a blade includes a laryngoscope blade.

As used herein, "artificial intelligence" or "AI" corresponds to intelligence demonstrated by machines, in contrast to the natural intelligence displayed by humans. As used herein, AI is used to describe machines (or computing devices) that mimic "cognitive" functions that humans associate with the human mind, such as "learning" and "problem solving." In the present case, AI refers to Analytical AI having characteristics consistent with cognitive intelligence, generating cognitive representation of the world, and using learning based on past experience to inform future decisions.

As used herein, the term "blockchain" refers to a time-dependent growing list of immutable informational objects or records (hereinafter referred to as "blocks") that are linked via cryptography. As used herein, the term "timestamp" refers to a sequence of characters or encoded information identifying when a certain event occurred. The timestamp includes digital date and time information that can be attached to the block. As used herein, the terms "hash" or "hash value" refer to a value resulting from a hash function, which is a function used to map certain data having an arbitrary size to data of a finite size. The hash is a unique identifier associated to a block, and is a key element of the distributed validated system described here. Typically, each block is associated with a timestamp, a hash of the then current block, and a hash associated with the immediately recent block of the then current block.

As used herein, "in situ" is understood to correspond to the chemical or physical sensing of the relevant byproducts in real time or substantially real time in the location where the system is positioned. For example, the system may be positioned in a chamber or the system may be positioned in proximity to a wound.

As defined herein, a "chamber" includes, but is not limited to, a refrigerator (commercial or residential), a freezer (commercial or residential), a cooler, a package truck, a package, a carton, a box, a shipping container, a pantry, metal cans, plastic bottles, plastic containers, plastic bags, glass containers, glass bottles, paper containers (waxed or unwaxed), a shelf, a wine cellar, a dehydrator, a medical device storage unit, a medical probe storage unit, an oil container, and storage rooms or area close to a wound in case of an intelligent bandage.

As referred to herein, the terms "computing device" and "entities" should be broadly construed and should be understood to be interchangeable. They may include any type of computing device, for example, a server, a desktop computer, a laptop computer, a smart phone, a cell phone, a pager, a personal digital assistant (PDA, e.g., with GPRS NIC), a mobile computer with a smartphone client, or the like. As defined herein, a "smart device" includes, but is not limited to, a smartphone, tablet, laptop or other computing device. Computing devices can be wired- or wireless-enabled, and can automatically discover, and pair with a plurality of other wireless-enabled devices.

As used herein, a "photoresistor" is intended to be synonymous with a "phototransistor," a "light-dependent resistor (LDR)," and a "photo-conductive cell," each one being a light-controlled variable resistor.

As used herein, "turbidity" is intended to be synonymous with "opacity," "milkiness," and "opalescence."

It should be appreciated by the person skilled in the art that 0 NTU, or 0% opacity, is considered "turbidity" for the purposes of this application. In one embodiment, the detection system and process of using same is intended to provide the user with an indication of perishable product freshness, or food spoilage, based on turbidity. In the case of 0 NTU, or 0% opacity, the perishable product is very fresh and has not undergone any measurable spoilage and the user may be interested in this information as well.

It should also be appreciated by the person skilled in the art that the term "shelf life" has many meanings, however, for the purposes of this application, "shelf life" corresponds to a point in the deterioration of the perishable product wherein the microbial activity has become dangerous for ingestion or consumption of said perishable product or for maintenance of the bandage on an animal, e g, a human.

As used herein, "microbial activity" refers to a physical change or a chemical change on or in the perishable product. Physical change includes, but is not limited to, a change in temperature, pressure, shape, size, color or growth of living organisms (e.g., bacteria, fungus, etc.). Chemical change includes, but is not limited to, the evolution of carbon dioxide, oxygen, *E. coli, salmonella, listeria*, volatile acids and bases, non-volatile acids and bases, slime formation, volatile and non volatile amines, or growth of living organisms (bacteria, fungus, etc.). It should be appreciated that microbial activity can result in microbial growth on or in the perishable product, which can eventually lead to spoilage and/or a decision about whether the perishable product, e.g., a medical device, be thoroughly sterilized before further use or that the perishable product, e.g., food, be disposed of.

The terms "good" and "bad" pertaining to ingestible products are understood to mean the product can be consumed or should not be consumed, respectively. As used herein, "bad" and "spoiled" are intended to be synonymous.

The present invention relates broadly to the detection of species that are by-products of microbial decay. The by-products of microbial decay can be a reactant in a chemical reaction, whereby the products of the chemical reaction are detectable. Once the information from the detector is discerned, the information can be analyzed, digitized and transmitted to a data processing unit and/or digital receiver, such as, for example, a wireless device, computing device, phone, or other data processing or communication device. Using the system and method described herein, once an unacceptable amount of microbial decay has been detected, as evidenced by an amount of byproduct sensed by the chemical sensor, a decision can be made regarding the disposal or sterilization of the perishable product as well as prioritizing usage or consumption.

Notably, the present invention does not relate to a food storage device management system to assist a person with finding the exact or approximate storage location of a certain food in their storage devices (e.g., where the milk is located in the refrigerator), nor does the present invention rely on visual indicators such as photographic and/or video images to determine if the food looks as though it is of low quality. In fact, taking a picture or video to conclude that the food is of low-quality disregards the fact that the food may still be consumable. The present invention relates to the reduction of food waste, wherein the metric for disposal is microbial growth, not that the banana looks brown, i.e., of kw quality. Accordingly, the system and method of using same does not require the use of cameras or photographs to identify microbial growth on or in the perishable product or where a specific product is in a storage device. It should be appreciated by the person skilled in the arts that a camera can still be present in the system described m the present application, for example, for use as a detector of backscattered light, forward scattered light, and transmitted light, as described herein.

Broadly, referring to FIG. 1, the microbial growth detection system 150 described herein comprises a physical or chemical sensor 152, a detection device capable of identifying a change of the respective sensor (e.g., change in turbidity or opacity) and converting the change into an electrical signal (e.g., emf or frequency) 153, a system that relays the electrical signal from the detection device to a digital output for analysis 154, and a display of the results of the analysis of the digital output 155 so as to communicate to a user the extent of microbial growth (i.e., is the perishable product spoiled or not). The microbial growth detection system can provide quantitative and/or qualitative results relating to microbial activity on or in a perishable product as well as convey activity data in formats for decision making. This system and method can be used in every aspect of the perishable product value chain, as a way to detect byproducts of microbial growth and thus indicators of integrity, for perishable product waste reduction, for product tracking, for automated inventory management, for inventory management in places with restricted visibility like vending machines, and freezers and large refrigerators. The system and method of using same can also be used for item level tagging for monitoring shelf life and compliance with safety as well as in dressing wounds in medical applications.

Figure 2A:
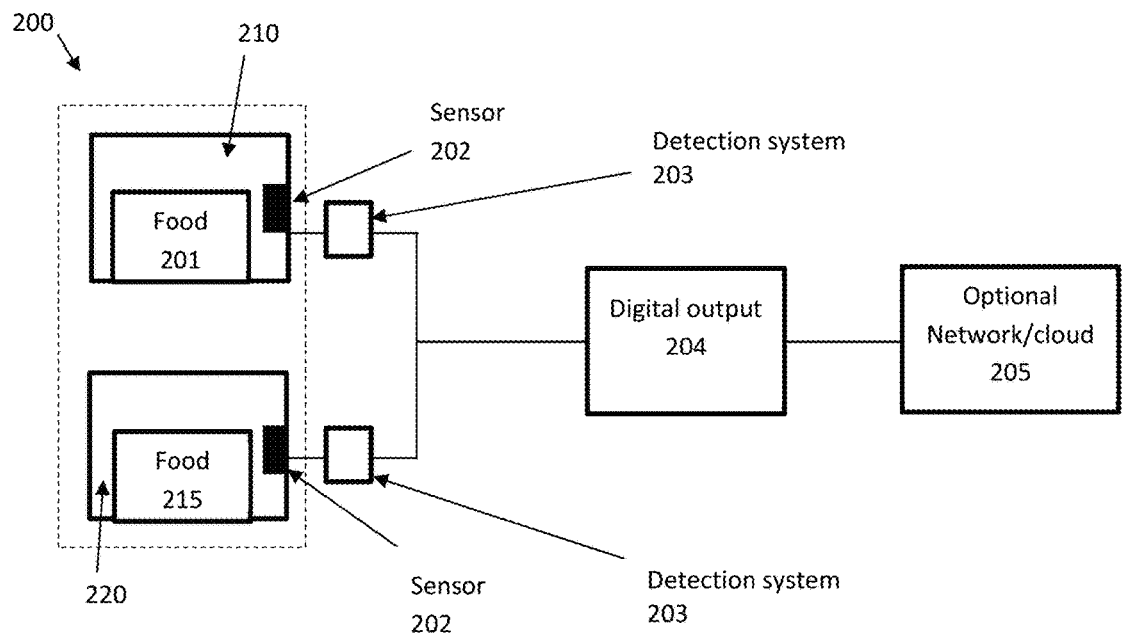
FIG. 2A is a schematic of an embodiment of the microbial growth detection system, or Microbial Activity Detection (MAD) (200) described herein.
Figure 2B:
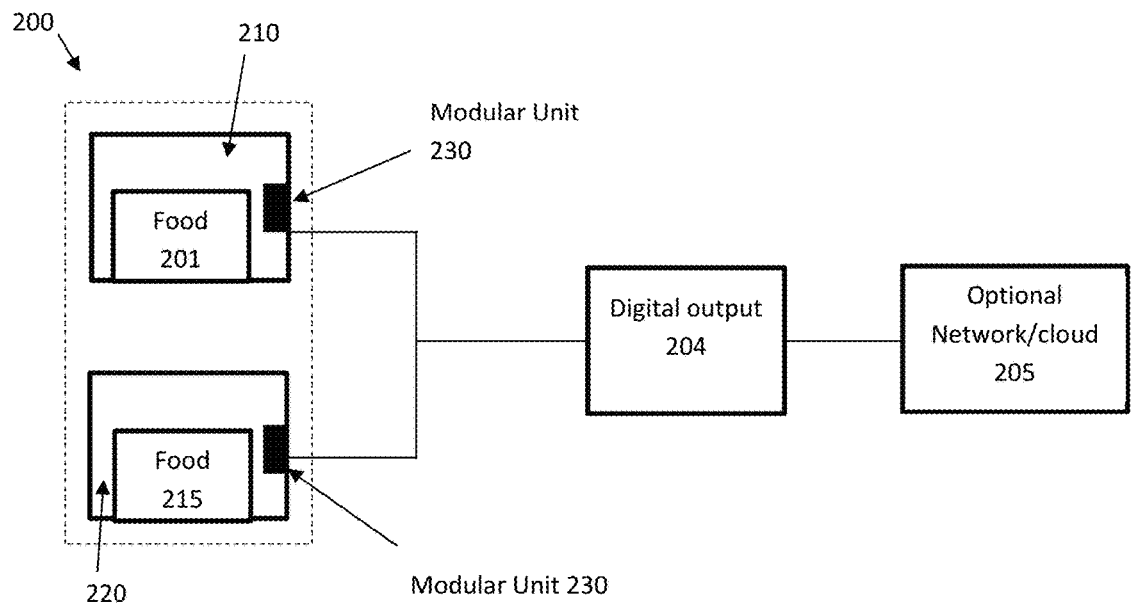
FIG. 2B is a schematic of another embodiment of the microbial growth detection system, or Microbial Activity Detection (MAD) (200) described herein.

The microbial growth detection system, also referred to as a Microbial Activity Detection (MAD) (200), is illustrated schematically in FIGS. 2A-B. In FIG. 2A, 201 represents the perishable product present in a chamber 210, e.g., a refrigerator, package, carton, or positioned over, or in proximity of, a wound, etc. A physical or chemical sensor 202 is also present in the chamber. The sensor 202 can comprise a sensor that is designed to detect byproducts of microbial growth including, but not limited to, $CO_2$, ethylene, hydrogen sulfide, ammonia, amines, total volatile nitrogen, and volatile acids and bases. Sensors can be flexible, screen-printed, single sensors or an array of sensors, or immobilized on a substrate, as readily understood to the skilled artisan. In a particularly preferred embodiment, a $CO_2$ sensor is used. A detection device 203 is included to permit the detection of changes in the sensor 202. The information from the detection device 203 is digitized and sent to a digital output device 204. The information from the detection device 203 can be sent using a wired format or wireless systems such as WiFi, BLUETOOTH®, or combination thereof. The digital output device 204 interprets or analyzes the data received from the detection device 203, using computing devices and algorithms, and is configured to provide an indication of the extent of microbial growth or the shelf-life status. For example, the digital output device 204 can be configured to display, on an output display, final results in analog (yes/no, green/yellow/red) or digital (food about to go bad or the consumption of a certain food should be prioritized over another food) format on a computing device or any smart device. The display can be in multiple languages. The digital output device 204 is optionally connected to a network or a cloud-based system, e.g., for inventory tracking, blockchain, and/or machine learning purposes, as understood by the person skilled in the art.

It is noted from FIG. 2A that a second chamber 220 comprising a perishable product 215, a sensor 202, and a detection device 203, is configured to optionally communicate, via wired formats or wireless systems, with the digital output device 204. It should be appreciated that chamber 201 and chamber 220 can be positioned in a larger, third chamber (shown schematically as a dashed line), or alternatively, chamber 201 and chamber 220 can represent entirely separate chambers. An example of the third chamber could be a refrigerator, wherein chamber 201 and chamber 220 represent two separate chambers that are being monitored within the third chamber refrigerator. Entirely separate chambers could be, for example, two separate refrigerators 201 and 220. It should be appreciated by the person skilled in the art that these are just examples to assist with the understanding of FIG. 2A and are not intended to limit the breadth of the MAD system in any way. It should also be appreciated to the person skilled in the art that perishable product 201 and perishable product 215 can be the same as or different from one another.

Detection systems 203 contemplated include, but are not limited to, at least one of a spectrophotometer, devices that utilize visual inspection, electromotive force (emf) detection, frequency detection, infrared detection, or any combination thereof. Alternative detection systems include, but are not limited to, fluorescent detectors, electrochemical detectors, dye-based detectors, and colorimetric indicator detectors, which are selected based on the byproduct of microbial growth to be detected. In a particularly preferred embodiment, the detection device comprises the emf detection or frequency detection. The detection device 203 further comprises a system that is capable of transmitting the digitized results to the digital output device 204, whether utilizing a wired format or wireless capabilities. In a preferred embodiment, the detection device comprises emf or frequency detection. For example, the detection device can detect turbidity/opacity in the detection device and can correlate the turbidity/opacity to a voltage or frequency measurement (i.e., an electrical signal).

In an embodiment of FIG. 2A, the sensor 202 comprises a cuvette holder for the insertion of a cuvette therein. The detection device 203 comprises a source of EMR, e.g., a LED, a photodetector, e.g., a photoresistor, and an MCU (micro-control unit), wherein the MCU comprises electronic circuitry and computer-executable instructions to digitize the detected changes in the sensor 202 to frequency or electromotive force and permit the relay of the digital data to a digital output device 204. The detection device 203 further comprises an energy source, including, but not limited to, batteries, RFID tags, NFID tags, and AC sources. The detection device may optionally include a temperature sensor in proximity of the cuvette holder, wherein the temperature sensor may detect ambient temperature and the temperature data is used in the determination of the byproduct quantification, the respiration quotient, and in the algorithms associated with the digital output 204. Additional temperature sensors are contemplated in the system, for example, on or in at least one of 201, 202, and/or 215. The detection device may optionally include a humidity detector, wherein the humidity sensor is preferentially located in proximity to the cuvette holder. Humidity can be relevant to the quantification of the byproduct quantification as well as the respiration quotient.

Although not intending to be bound by a numerical value, the system can be programmed to detect the extent of microbial growth at least one time per day, for example, 2, 3, 4, 5, 6, 7, 8, 9, 10, or more readings per day, as readily determined by the person skilled in the art.

In a first aspect, a system for detecting microbial growth on or in at least one perishable product in real time is described, said system comprising:
(A) a chemical sensor comprising a cuvette holder for the positioning of a cuvette, wherein the chemical sensor is capable of sensing a byproduct of microbial growth;
(B) a detection device for measuring at least one characteristic of said chemical sensor and converting the measured characteristic into an electrical signal;
(C) a digital output device capable of receiving the electrical signal from the detection device and algorithmically analyzing the electrical signal; and
(D) an output display, wherein results of the analysis performed by the digital output device are provided to a user, wherein the results convey to the user the extent of microbial growth of the perishable product.

The detection device can digitize the relative light opacity (or color) of the solution in the cuvette to frequency or electromotive force (i.e., an electrical signal). The digital output device uses an algorithm to correlate the electrical signal from the detection device to the extent of microbial growth for the perishable product. Once the extent of microbial growth on or in the perishable product becomes too large, as readily identified by the digital output device using algorithms, the output display is configured to warn the user that a decision must be made including, but not limited to, the approximate shelf-life remaining, disposal of the perishable product, imminent ingestion or consumption of the perishable product, or sterilization of the medical device. In practice, the system will further comprise a cuvette, which is insertable in the cuvette holder, wherein the cuvette comprises at least one species that reacts with the byproduct of microbial growth. In one embodiment, the cuvette comprises at least one wall comprising a gas-permeable microporous membrane capable of byproduct diffusion therethrough, and at least one wall that is optically transparent in the wavelengths employed in the method of using the microbial growth detection system. The detection device further comprises a source of electromagnetic radiation (EMR), such as a light-emitting diode (LED) or IR-emitting diode. In one embodiment, the detection device in the first aspect is the one described herein in the fourth aspect. In one embodiment, the cuvette holder is the one described herein in the fifth aspect.

In a preferred embodiment of the first aspect, the system for detecting microbial growth on or in at least one perishable product in real time comprises:
- (A) a carbon dioxide sensor comprising a cuvette holder for the positioning of a cuvette, wherein the $CO_2$ sensor is capable of sensing carbon dioxide emanating from the perishable product;
- (B) a detection device for measuring turbidity in the $CO_2$ sensor and converting the turbidity into an electrical signal;
- (C) a digital output device capable of receiving the electrical signal from the detection device and algorithmically analyzing the electrical signal; and
- (D) an output display, wherein results of the analysis performed by the digital output device are provided to a user, wherein the results convey to the user the extent of microbial growth of the perishable product.

The detection device can digitize the relative light opacity (or color) of the solution in the cuvette to frequency or electromotive force (i.e., an electrical signal). The digital output device uses an algorithm to correlate the electrical signal from the detection device to the extent of microbial growth for the perishable product. Once the extent of microbial growth on or in the perishable product becomes too large, as readily identified by the digital output device using algorithms, the output display is configured to warn the user that a decision must be made including, but not limited to, the approximate shelf-life remaining, disposal of the perishable product, imminent ingestion or consumption of the perishable product, or sterilization of the medical device. In practice, the system will further comprise a cuvette, which is insertable in the cuvette holder, wherein the cuvette comprises at least one species that reacts with the byproduct of microbial growth. For example, when sensing $CO_2$, the at least one species can comprise an aqueous hydroxide solution such as calcium hydroxide. In one embodiment, the cuvette comprises at least one wall comprising a gas-permeable microporous membrane capable of $CO_2$ diffusion therethrough, and at least one wall that is optically transparent in the wavelengths employed in the method of using the microbial growth detection system. The detection device further comprises a source of electromagnetic radiation (EMR). In one embodiment, the detection device in the first aspect is the one described herein in the fourth aspect. In one embodiment, the cuvette holder is the one described herein in the fifth aspect.

"Users" of the system include, but are not limited to, farmers, processors, distributors, manufacturers, storage operators, transporters, retail stores, food service operations, members of households, and medical service providers.

Advantageously, the microbial growth detection system can detect microbial growth in real time. In some embodiments, the microbial growth detection system can detect microbial growth in situ in real time. The system is compact, sensitive, inexpensive, automated, and easy to use. The system is universal and as such, does not have to be tailored to the perishable product, with the proviso that the size and/or arrangement of the overall system may have to be adapted because of perishable product environment requirements (e.g., a refrigerator versus a wound). Furthermore, the microbial growth detection system can provide an output display, or a response, that is qualitative or quantitative and analog or digital. For example, the response can comprise a color scheme (e.g., green, red, orange, wherein a color indicates whether the food has spoiled), text or numerical data. This output data can be further used for machine learning and artificial intelligence to improve the system and method of using.

Additional advantages associated with the microbial growth system described herein is the ability to trace and manage perishable products, including status alerts and prioritization of activities such as using a particular food before it spoils or changing a bandage on a wound because the microbial growth is excessive, and can be applied in a variety of industries including, but not limited to, food, medicine, medical devices, beauty, and hygiene products. This invention can predict the status of microbial growth in real time by measuring chemicals released during microbial activity. The output from the sensor data can be correlated to the extent of microbial activity, and provide information to the user through, for example, their smart devices.

Further advantages of the microbial system described herein is that no sample preparation or technical training is necessary, and the system can be single use or reusable. It should be appreciated that the chemical species in the chemical sensor may be prepared by the user but in many scenarios, a manufacturer will prepare and provide the chemical species to the user. For example, the system comprises a chemical sensor comprising a cuvette holder for the positioning of a cuvette. The cuvette comprises at least one species that reacts with the byproduct of microbial growth, as discussed further hereinbelow. If the species undergoes an irreversible reaction, the contents of the cuvette cannot be reused. Accordingly, the system comprises a cuvette holder wherein cuvettes comprising fresh chemistries (i.e., reactants for the chemical reaction) can be inserted therein and withdrawn at the completion of the chemical reaction, for reuse of the system.

Modular Unit

Figure 3A:
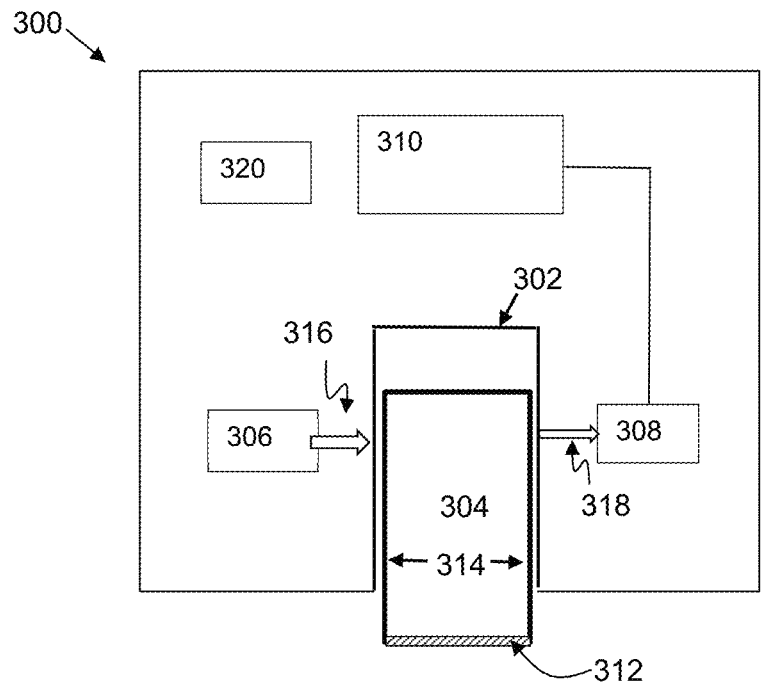
FIG. 3A is a schematic of an embodiment of the modular unit described herein, wherein the cuvette is partially inserted in the cuvette holder.
Figure 3B:
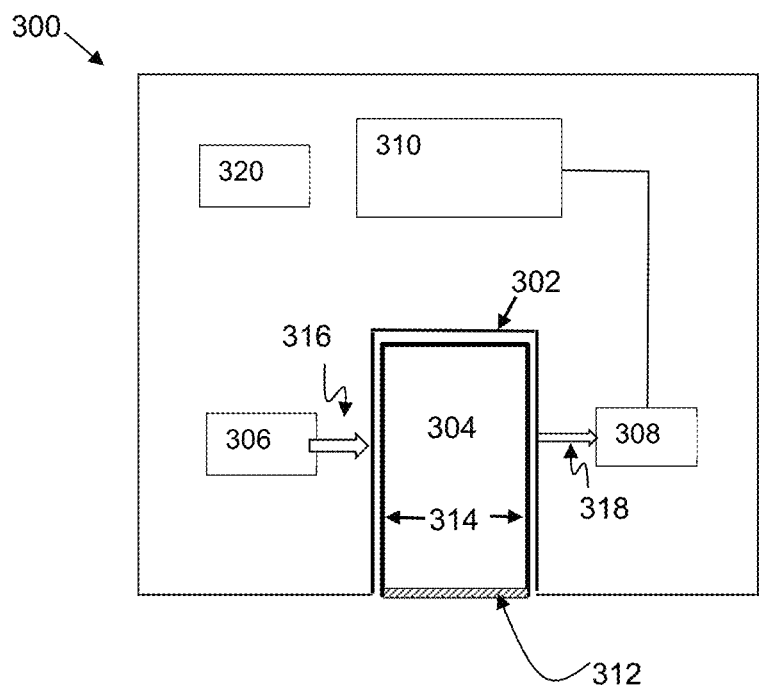
FIG. 3B is a schematic of another embodiment of the modular unit described herein, wherein the cuvette is fully inserted in the cuvette holder.
Figure 3C:
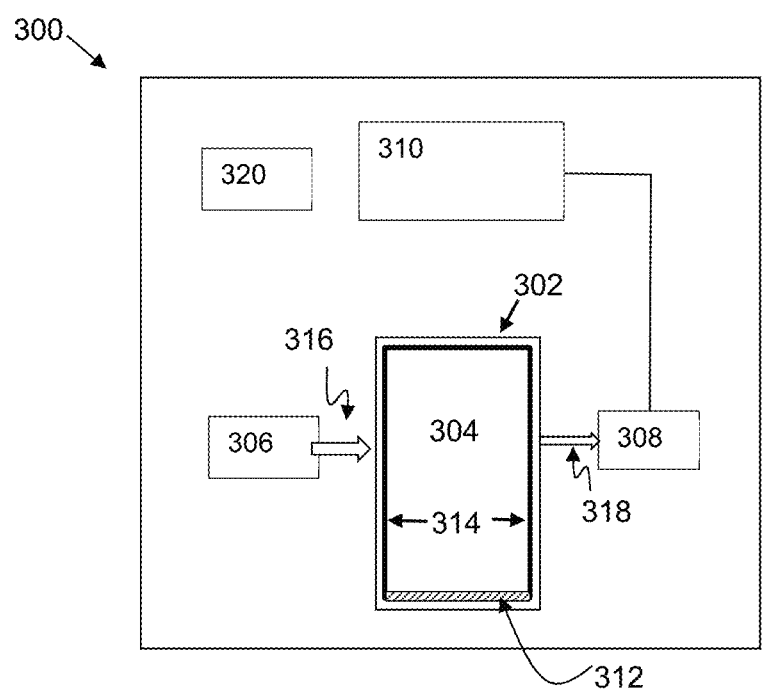
FIG. 3C is a schematic of another embodiment of the modular unit described herein, wherein the cuvette is positioned on the inside of the enclosure of the modular unit.

As introduced hereinabove with reference to FIG. 2A, the detection device 203 is included to permit the detection of changes in the sensor 202. Although shown outside of the chamber 210 in FIG. 2A, the detection device 203 is preferably positioned in a modular unit or housing 300 that also comprises the sensor 202, wherein the modular unit is present inside the chamber 210, 220 (FIG. 2B). Embodiments of the modular unit 300 are illustrated in FIGS. 3A-C. It should be appreciated by the person skilled in the art that the arrangement of the modular unit is not limited to that shown in FIGS. 3A-C, and is intended to be broadly interpreted. The modular unit 300 comprises a cuvette holder 302, wherein the partial insertion of a cuvette 304 in the holder 302 is illustrated in FIG. 3A. The modular unit further comprises a source of EMR 306, e.g., a LED, and a photodetector 308, e.g., a photoresistor. The incident light 316 from the source EMR 306 passes through a small cavity (not shown) in the cuvette holder 302 and the walls of the cuvette 304, which are optically transparent in the wavelengths employed in the method of detecting microbial growth, and emerges from another small cavity (not shown) in the cuvette holder as transmitted light 318. The MCU (micro-control unit) 310 comprises electronic circuitry and computer-executable instructions to digitize the relative light opacity (or color) of the solution in the cuvette to frequency or electromotive force and permit the relay of the digital data to a digital output device. The modular unit further comprises an energy source 320 including, but not limited to, batteries, RFID tags, NFID tags, and AC sources. The modular unit 300 preferably comprises an enclosure that minimizes the exposure of the components contained therein to external light and noise, which can interfere with the measurement of the turbidity/opacity of the solution in the cuvette 304.

FIG. 3B illustrates the full insertion of the cuvette in the modular unit of FIG. 3A, wherein the semipermeable membrane of the cuvette is directly exposed to the environment outside of the modular unit. FIG. 3C represents another embodiment of the modular unit, wherein the cuvette holder and cuvette are positioned within the enclosure of the modular unit, wherein the enclosure is fabricated using a material that permits the passage or permeability of gases therethrough. It is understood that the enclosure of FIG. 3C may have an access or door to access the cuvette in the event the cuvette is to be replaced for reuse of the modular unit. Alternatively, the enclosure of FIG. 3C can be fully disposable and hence devoid of any access or door to access the inside of the modular unit.

It should be appreciated by the person skilled in the art that although only one wall of the cuvette in FIGS. 3A-3C comprises a gas-permeable microporous membrane capable of byproduct diffusion therethrough, that the invention is not intended to be limited as such. In one embodiment, at least two walls of the cuvette comprise a gas-permeable microporous membrane capable of byproduct diffusion therethrough. Further, at least two walls of the cuvette can be optically transparent in the wavelengths employed in the method of using the microbial growth detection system.

The modular unit may optionally incorporate a RFID tag or an SKU tag or any other tags with functionality of product tracking (e.g., date, location, weight, etc.) to allow a user, e.g., a farmer, distributor, consumer, having more than one microbial growth detection systems to identify and monitor the location and current condition of the microbial growth detection system. The RFID tags may communicate with an RFID reader and/or sensor network access point. Each RFID tag may include a controller, a sensor and memory, which are preferably embodied on a single chip, but may also or alternatively include a different type of controller, such as an application specific integrated circuit (ASIC). The RFID tags may optionally be BLUETOOTH®-enabled, ZigBee-enabled, WiFi-enabled, and/or cellular data-enabled.

In one embodiment, the enclosure is made using 3-D printing because of the flexibility of design, although other methods of fabricating the enclosure are contemplated. The size and the shape of the modular unit is entirely dependent on the environment that the modular unit is intended to be placed to sense and detect microbial growth. For example, the unit can be a cubic square or a rectangular parallelepiped with a size in a range from about 3-10 cm×about 3-10 cm×about 3-10 cm, as readily determined by the person skilled in the art. Alternatively, a unique modular unit can be designed and fabricated to specifically fit into a unique environment. For example, with the advent of 3-D printing, any shape and size of the enclosure is easily envisioned. The cuvette holder can accommodate a cuvette having, e.g., a circular cylinder, a cubic square, or a rectangular parallelepiped shape, as readily determined by the person skilled in the art.

As introduced hereinabove, the entire modular unit 300 comprising the sensor and the detection device is preferably positioned inside the chambers 210, 220. An embodiment of this is shown in FIG. 2B.

In a preferred embodiment, the modular unit comprises components that have low energy requirements and that do not emanate a substantial amount of heat during operation. It should be appreciated that if heat is generated in the modular unit that a fan or other cooling device may be included in the modular unit to manage the temperature or voltage fluctuations. Further, the modular unit can be produced inexpensively and can be adapted to fit in any environment where products undergo microbial growth and spoilage.

Accordingly, a second aspect of the invention relates to a modular unit comprising:

(i) a chemical sensor comprising a cuvette holder for the positioning of a cuvette, wherein the chemical sensor is capable of sensing a byproduct of microbial growth; and (ii) a detection device for measuring at least one characteristic of said chemical sensor and converting the measured characteristic into an electrical signal.

The detection device can digitize the relative light opacity (or color) of the solution in the cuvette to frequency or electromotive force (i.e., an electrical signal). In practice, the modular unit will further comprise a cuvette, which is insertable in the cuvette holder, wherein the cuvette comprises at least one species that reacts with the byproduct of microbial growth. In one embodiment, the cuvette comprises at least one wall comprising a gas-permeable microporous membrane capable of byproduct diffusion therethrough, and at least one wall that is optically transparent in the wavelengths employed. The detection device further comprises a source of electromagnetic radiation (EMR), such as a light-emitting diode (LED) or IR-emitting diode.

In a preferred embodiment of the second aspect of the invention, a modular unit comprises:

(i) a $CO_2$ sensor comprising a cuvette holder for the positioning of a cuvette, wherein the $CO_2$ sensor is capable of sensing $CO_2$ gas; and (ii) a detection device for measuring turbidity in the $CO_2$ sensor and converting the turbidity into an electrical signal.

The detection device can digitize the relative light opacity (or color) of the solution in the cuvette to frequency or electromotive force (i.e., an electrical signal). In practice, the modular unit will further comprise a cuvette, which is insertable in the cuvette holder, wherein the cuvette comprises at least one species that reacts with the byproduct of microbial growth. In one embodiment, the cuvette comprises at least one wall comprising a gas-permeable microporous membrane capable of byproduct diffusion therethrough, and at least one wall that is optically transparent in the wavelengths employed. The detection device further comprises a source of electromagnetic radiation (EMR), such as a light-emitting diode (LED) or IR-emitting diode.

In a third aspect, a system for detecting microbial growth on or in a perishable product in real time is described, said system comprising:
- (A) modular unit comprising:
  - (i) a chemical sensor comprising a cuvette holder for the positioning of a cuvette, wherein the chemical sensor is capable of sensing a byproduct of microbial growth; and
  - (ii) a detection device for measuring at least one characteristic of said chemical sensor and converting the measured characteristic into an electrical signal;
- (B) a digital output device capable of receiving the electrical signal from the detection device and algorithmically analyzing the electrical signal; and
- (C) an output display, wherein results of the analysis performed by the digital output device are provided to a user, wherein the results convey to the user the extent of microbial growth of the perishable product.

The detection device can digitize the relative light opacity (or color) of the solution in the cuvette to frequency or electromotive force (i.e., an electrical signal). The digital output device uses an algorithm to correlate the electrical signal from the detection device to the extent of microbial growth for the perishable product. Once the extent of microbial growth on or in the perishable product becomes too large, as readily identified by the digital output device using algorithms, the output display is configured to warn the user that a decision must be made including, but not limited to, the approximate shelf-life remaining, disposal of the perishable product, imminent ingestion or consumption of the perishable product, or sterilization of the medical device. In practice, the system will further comprise a cuvette, which is insertable in the cuvette holder, wherein the cuvette comprises at least one species that reacts with the byproduct of microbial growth. In one embodiment, the cuvette comprises at least one wall comprising a gas-permeable microporous membrane capable of byproduct diffusion therethrough, and at least one wall that is optically transparent in the wavelengths employed in the method of using the microbial growth detection system. The detection device further comprises a source of electromagnetic radiation (EMR), such as a light-emitting diode (LED) or IR-emitting diode. In one embodiment, the detection device in the third aspect is the one described herein in the fourth aspect. In one embodiment, the cuvette holder is the one described herein in the fifth aspect.

In a preferred embodiment of the third aspect, the system for detecting microbial growth on or in a perishable product in real time comprises:
- (A) a modular unit comprising:
  - (i) a carbon dioxide sensor comprising a cuvette holder for the positioning of a cuvette, wherein the $CO_2$ sensor is capable of sensing carbon dioxide emanating from the perishable product;
  - (ii) a detection device for measuring turbidity in the chemical sensor and converting the turbidity into an electrical signal;
- (B) a digital output device capable of receiving the electrical signal from the detection device and algorithmically analyzing the electrical signal; and
- (C) an output display, wherein results of the analysis performed by the digital output device are provided to a user, wherein the results convey to the user the extent of microbial growth of the perishable product.

The detection device can digitize the relative light opacity (or color) of the solution in the cuvette to frequency or electromotive force (i.e., an electrical signal). The digital output device uses an algorithm to correlate the electrical signal from the detection device to the extent of microbial growth for the perishable product. Once the extent of microbial growth on or in the perishable product becomes too large, as readily identified by the digital output device using algorithms, the output display is configured to warn the user that a decision must be made including, but not limited to, the approximate shelf-life remaining, disposal of the perishable product, imminent ingestion or consumption of the perishable product, or sterilization of the medical device. In practice, the system will further comprise a cuvette, which is insertable in the cuvette holder, wherein the cuvette comprises at least one species that reacts with the byproduct of microbial growth. For example, when sensing $CO_2$, the at least one species can comprise an aqueous hydroxide solution such as calcium hydroxide. In one embodiment, the cuvette comprises at least one wall comprising a gas-permeable microporous membrane capable of $CO_2$ diffusion therethrough, and at least one wall that is optically transparent in the wavelengths employed in the method of using the microbial growth detection system. The detection device further comprises a source of electromagnetic radiation (EMR). In one embodiment, the detection device in the third aspect is the one described herein in the fourth aspect. In one embodiment, the cuvette holder is the one described herein in the fifth aspect.

Advantageously, the modular unit of the second and third aspect is based on spectrophotometric principles without requiring the use of a traditional spectrophotometer. Accordingly, it can have a small footprint and can be placed in environments that a traditional spectrophotometer cannot be placed. In addition, the modular unit is simple to use and no sample preparation is needed and as such, the modular unit does not require a specially trained technician to operate same. Moreover, the cost of the modular unit is a fraction of the cost of a traditional spectrophotometer.

An Embodiment of a Sensor

An embodiment of a sensor for the microbial growth detection system includes a chemical sensor, for example, a $CO_2$ sensor. It is possible to reliably detect low amounts of $CO_2$ released during microbial growth in real time from a perishable product. A $CO_2$ sensor exploits the principles of chemical kinetics to produce a change in the appearance of a chemical solution when the carbon dioxide comes in contact with the chemical solution. The output of the sensor can be measured as change in opacity and can be quantified as the concentration of carbon dioxide released from the perishable product during microbial growth.

The $CO_2$ sensor uses a cuvette 304 comprising at least one wall comprising a gas-permeable microporous membrane 312 capable of $CO_2$ diffusion therethrough, and at least one wall that is optically transparent 314 in the wavelengths employed in the method of using the microbial growth detection system. As understood by the person skilled in the art, the shape of the cuvette should substantially correspond to the shape of the cuvette holder in the modular unit so that the cuvette is insertable in the cuvette holder.

The $CO_2$ sensor uses a gas-permeable microporous membrane to permit $CO_2$ gas to contact the chemical solution contained in the cuvette. Preferably, liquids and solids cannot penetrate the microporous membrane. Even more preferably, the microporous membrane is permeable to only $CO_2$ gas. As a result, the acidity or alkalinity of the perishable product does not affect the $CO_2$ sensor. Further, the $CO_2$ sensor is usable with perishable products regardless of the temperature, humidity, and/or pressure conditions to which they may be subjected during manufacture, handling, and distribution. When fully inserted in the modular unit, only the $CO_2$-permeable microporous membrane 312 is in contact with the environment comprising the perishable product (312). $CO_2$-permeable microporous membranes include, but are not limited to, fluorinated ethylene propylene having a specific gravity of approximately 2, polyvinyl chloride copolymer, any microporous sheet that is $CO_2$-permeable, and commercially available microporous sheets that are colored and are safe for human use. Fluorinated ethylene propylene, also known as TEFLON™, can be selected to have a pore size large enough to pass carbon dioxide gas but too small to pass liquids.

The cuvette, other than the gas-permeable microporous membrane, comprises at least one inert material selected from plastic, glass, and quartz, preferably quartz. A chemical sensing solution is introduced to the cuvette and the cuvette sealed, wherein the semipermeable membrane is bound to an opening of the cuvette using an adhesive which is impervious to a chemical sensing solution comprised therein. The solution provides an observable change when the concentration of $CO_2$ rises substantially, above that which is the normal ambient concentration of $CO_2$ for our atmosphere. In the preferred embodiment, the chemical sensing solution is an aqueous solution and comprises at least one species selected from the group consisting of beryllium hydroxide, calcium hydroxide, magnesium hydroxide, strontium hydroxide, barium hydroxide, ammonium hydroxide, lithium hydroxide, sodium hydroxide, potassium hydroxide, potassium carbonate, sodium barbitol, tribasic sodium phosphate, dibasic sodium phosphate, potassium acetate, monoethanolamine, diethanolamine, piperidine, and any combination thereof, preferably a hydroxide salt, more preferably a Group II hydroxide salt including, but not limited to, beryllium hydroxide, calcium hydroxide, magnesium hydroxide, strontium hydroxide, barium hydroxide, and any combination thereof. In a particularly preferred embodiment, the chemical sensing solution comprises calcium hydroxide, which has USDA approval for human consumption, and which upon contact with $CO_2$, forms calcium carbonate, a white precipitate. The concentration of hydroxide salt in the cuvette is in a range from about 0.001 M tri about 5 M, preferably about 0.05 M to about 2 M, and more preferably about 0.10 m to about 0.50 M. For example, a molarity in the concentration range of 0.1-0.5 M $Ca(OH)_2$ requires approximately 5% $CO_2$ gas concentration to initiate precipitation of calcium carbonate. Since the atmospheric concentration of carbon dioxide is approximately 0.3%, atmospheric $CO_2$ will not affect $CO_2$ sensors in the concentration range of 0.1-0.5 M which are left exposed to the air. Further, since the microporous membrane is liquid impermeable, the calcium hydroxide solution will not dry out from storage under exposure to the atmosphere. In one embodiment, said sensor for detecting $CO_2$ is in a concentration range wherein said at least one characteristic, e.g., turbidity, varies in a defined mathematical relationship with an increase in $CO_2$ concentration in said enclosed chamber for the perishable product. The defined relationship is linear, exponential, logarithmic, quadratic, binomial, virial, differential, or a computer-based curve fit.

It is understood by the person skilled in the art that the $CaCO_3$ precipitate may settle over time, which will impact the accuracy of the sensor. Accordingly, in another embodiment, the cuvette and/or cuvette holder further comprises an agitator for stirring/agitating the solution contained within the cuvette, said agitator including, but not limited to, a mixer, a magnetic stirrer coupled with a spinning magnet, a propeller, a vibrator, a sonicator, and combinations thereof.

Preferably, the cuvette is agitated at some time prior to the measurement of turbidity. The incorporation of an agitator, as well as the preferred time of agitation, is well understood to the person skilled in the art.

Because the human eye is unable to adequately quantify the extent of $CaCO_3$ precipitation, i.e., turbidity, the present microbial growth detection system represents a substantial improvement over the prior art, using spectiophotometric principles to detect turbidity. Unlike the spectrophotometers known in the art, which are expensive and bulky, the present system uses a detection system that is robust, inexpensive to make, and can be easily scaled to fit in any environment where products may undergo microbial growth, and hence spoilage. Moreover, using spectrophotometric principles and algorithms, the system can quantify the amount of $CO_2$ detected, rather than just visualizing that the solution is opaque, allowing for a more exact determination and quantification of whether a perishable product is spoiled or will be spoiled within a certain number of days under the current conditions.

In one embodiment of the described system, the hydroxide salt $CO_2$ sensor described herein does not rely on colorimetric principles, pH-sensitive indicators including, but not limited to, cresol red, metacresol purple. and the like. Put another way, the $CO_2$ sensor in this embodiment is substantially devoid of pH sensitive indicators and color changeable dyes. In another embodiment of the described system, the sensor may utilize colorimetric principles and/or pH-sensitive indicators, as readily understood by the person skilled in the art.

Alternatively, the detection device for the $CO_2$ sensor can detect another characteristic of the reaction including, but not limited to, NTU, milkiness, opalescence, redox potential change, or a color change. Other $CO_2$ sensors contemplated include, but are not limited to, a fluorescent sensor, an electrochemical sensor, a dye-based sensor, and a colorimetric-indicator sensor. The sensor for detecting $CO_2$ is optionally adsorbed onto a substrate.

Advantages of the $CO_2$ sensor described herein includes, but is not limited to, a sensor which is usable on a widest variety of locations, and usable in connection with the widest variety of perishable products; which provides an indication of microbial growth independently of the particular pH of the perishable product; which has a long shelf-life both before and after incorporation into a chamber comprising a perishable product; and which has a compact configuration leading to the widest utilization possible.

An Embodiment of a Detection Device

As broadly described above, the detection device 203 in FIG. 2A a source of light, e.g., a LED, and a detection device, e.g., a photoresistor, for measuring a change in the sensor 202. In addition, the modular unit or housing 230 in FIG. 2B comprises a cuvette holder, a source of light, e.g., a LED, and a detection device, e.g., a photoresistor, for measuring a change in the chemical sensor. Although not shown, the detection device can further include a temperature sensor and/or a humidity detector.

Figure 4:
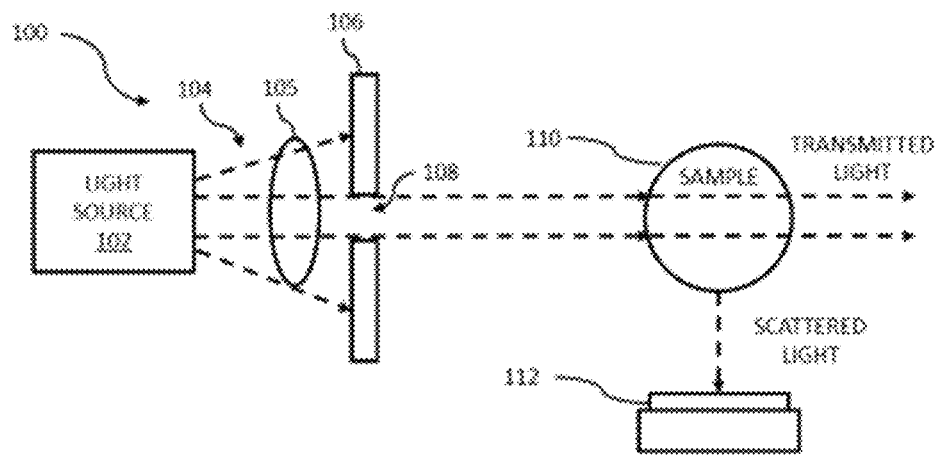
FIG. 4 is a schematic of an embodiment of a detection device 100 and sensor, for measuring turbidity.

FIG. 4 is a schematic of an embodiment of a detection device of the system described herein. Referring to FIG. 4, the detection device 100 includes a light source 102 configured to generate and to direct a light beam, generally indicated by broken line arrows 104, towards a shield 106. The light source 102 may comprise a light emitting diode (LED) or any other suitable source of light as will be appreciated by those of skill in the art. The frequency of light generated by the light source 102 may be a portion or the entirety of the infrared range or also portions of electromagnetic spectrum. The light beam 104 may be directed towards a lens 105 that focuses the light beam before the light reaches the shield 106. It is noted that the lens is optional, wherein an aperture in the cuvette holder directs the light to the sample, or alternatively, the lens may be replaced by another suitable optical device or mechanism for directing the generated light to the sample 110. The shield 106 defines an aperture 108 that allows for passage of some of the light towards a sample 110. The shield 106 may be a wall of a cuvette holder having an aperture defined therein for passage of light. The sample 110 may be a solution contained, for example, in the cuvette. In this example, the distance between the light source 102 and the center of the lens 105 is equal to or about equal to the focal length of the lens 105 such that light beams exiting the lens 105 are parallel, although the distance between the light source 102 and the lens 105 may be any other suitable distance.

Light incident upon the sample 110 may either transmit through the sample 110 or scatter. In this embodiment, a detector 112 may be positioned to receive at least a portion of the scattered light. The figure depicts the scattered light received by the detector 112 as being scattered at an angle of about 90°, although it should be appreciated that the detector 112 may be place in another suitable position for receiving scattered light from a different angle. The detector 112 may be a photodetector, photoresistor, or the like.

Although not shown in FIG. 4, the detector 112 may be operably connected to a suitable computing device having hardware, software, firmware, or a combination thereof for implementing functionality disclosed herein for analyzing the turbidity of the sample 110. An example equation that may be applied by the computing device for analyzing turbidity of the sample 110 follows:

$$T = d * I_{90}$$

where T represents turbidity in NTU, d represents calibration coefficient, and $I_{90}$ represents light intensity of 90°. A representation of the determined turbidity may be displayed or otherwise presented on a user interface controlled by the computing device.

It is noted that a detection device in accordance with embodiments of the present disclosure may include a microcomputer for controlling and receiving output signals from one or more light sources and one or more detectors as disclosed herein. Any suitable microcomputer may be utilized. For example, for experimentation a RASPBERRY PI® computing device, an ARDUINO® computing device, an Espressif Systems ESP 8266 microcontroller, an Espressif Systems ESP 32 microcontroller, or the like may be utilized.

Figure 5:
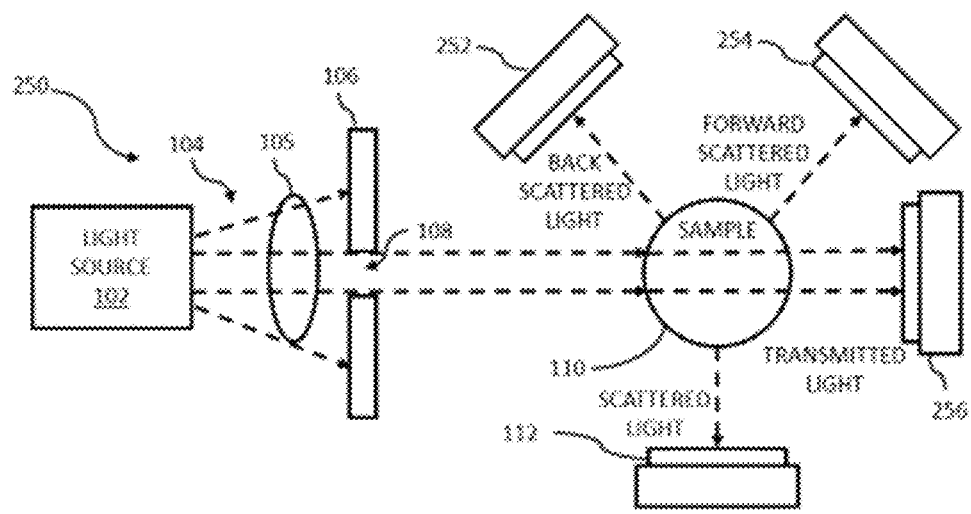
FIG. 5 is a schematic of another embodiment of a detection device 250 and sensor, for measuring turbidity.

FIG. 5 is a schematic of another embodiment of a detection device of the system described herein. Referring to FIG. 5, the detection device 250 is similar to the detection device 100 shown in FIG. 4. This type of detection device may be referred to as a "ratio-type turbidimeter." The detection device 250 includes the detector 112 for receipt of scattered light at 90° and also one or a combination of other detectors 252, 254, and 256 for receipt of backscattered light, forward scattered light, and transmitted light, respectively. The detectors 112, 252, 254, and 256 may be photodetectors, photoresistors, or the like. Similar to FIG. 4, it is noted that the lens is optional and may be replaced by another suitable optical device or mechanism for directing the generated light to the sample 110.

Although not shown in FIG. 5, the detectors 112, 252, 254, and 256 may be operably connected to a suitable computing device having hardware, software, firmware, or a combination thereof for implementing functionality disclosed herein for analyzing the turbidity of the sample 110. An example equation that may be applied by the computing device for analyzing turbidity of the sample 110 follows:

$$T = \frac{I_{90}}{d_t * I_t + d_{fs} * I_{fs} + d_{bs} * I_{bs} + d_{90} * I_{90}}$$

where T represents turbidity in NTU, d* represents calibration coefficient of each angle, t represents transmitted, fs represents forward scattered, bs represents backscattered, and I* represents light intensity of each angle. A representation of the determined turbidity may be displayed or otherwise presented on a user interface controlled by the computing device. It should be appreciated that the foregoing equation can be altered depending on which detectors are present in the detection device. For example, the foregoing equation is used when all four detectors 112, 252, 254, and 256 are online detecting light. The equation is easily altered if less than all four detectors are online detecting light. The person skilled in the art will readily determine which detectors must be used for the most accurate determination of turbidity or other measurable change.

Figure 6:
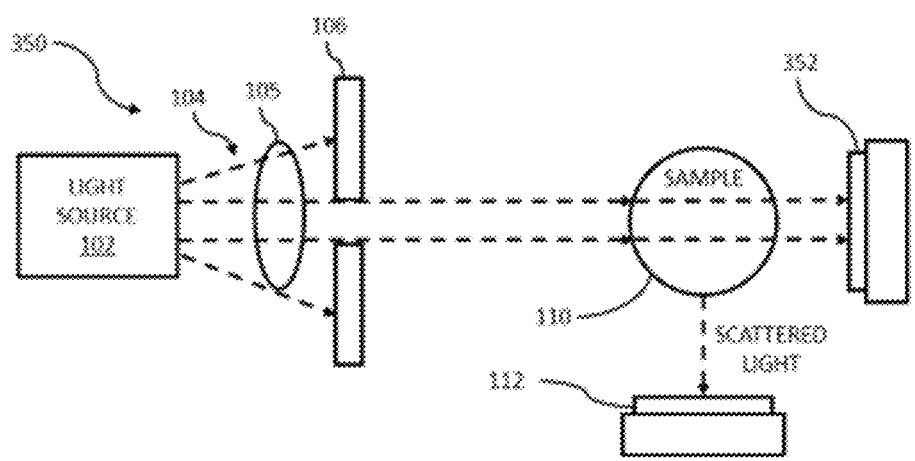
FIG. 6 is a schematic of another embodiment of a detection device 350 for measuring turbidity.

FIG. 6 is a schematic of another embodiment of a detection device of the system described herein. Referring to FIG. 6, the detection device 350 is similar to the detection device 100 shown in FIG. 4. This type of detection device may be referred to as an "arranged ratio turbidimeter". The detection device 350 includes the detector 112 for receipt of scattered light at 90° and another detector 352 for receipt of transmitted light. The detectors 112 and 352 may be photodetectors, photoresistors, or the like. Similar to FIG. 4, it is noted that the lens is optional and may be replaced by another suitable optical device or mechanism for directing the generated light to the sample 110.

Although not shown in FIG. 6, the detectors 112 and 352 may be operably connected to a suitable computing device having hardware, software, firmware, or a combination thereof for implementing functionality disclosed herein for analyzing the turbidity of the sample 110. An example equation that may be applied by the computing device for analyzing turbidity of the sample 110 follows:

$$T = \frac{I_{90}}{d_t * I_t + d_{90} * I_{90}}$$

where T represents turbidity in NTU, d* represents calibration coefficient of each angle, and I* represents light intensity of each angle. A representation of the determined turbidity may be displayed or otherwise presented on a user interface controlled by the computing device.

Figures 7A, 7B:
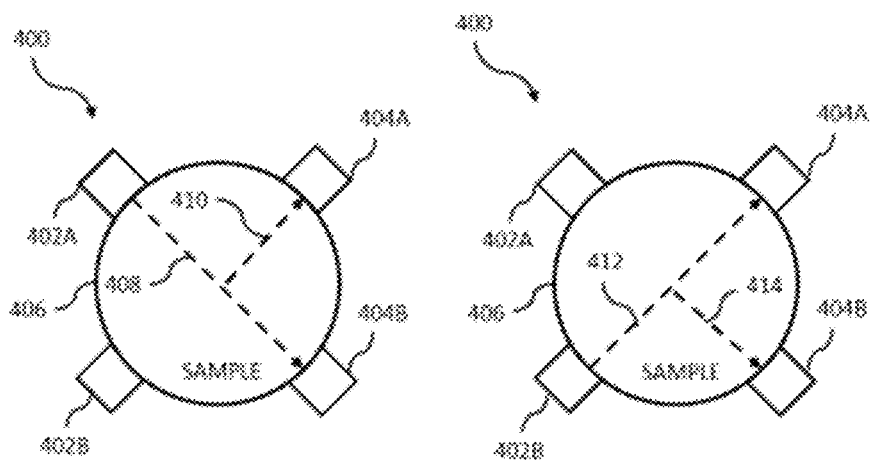
FIG. 7A is a schematic of another embodiment of a detection device 400 including two light sources 402A, 402B and two detectors 404A, and 404B for measuring turbidity.
FIG. 7B is a schematic of another embodiment of a detection device 400 including two light sources 402A, 402B and two detectors 404A, and 404B for measuring turbidity.

In another embodiment, a detection device comprises two or more light sources and two or more detectors. In an example, the detection device according to this embodiment may detect scattered light and transmitted light. FIG. 7A is a schematic of another embodiment of a detection device 400, or turbidimeter, including two light sources 402A, 402B and two detectors 404A, and 404B for measuring turbidity. Detection device 400 detects scattered light at 90° and transmitted light at 180°. The detectors 404A, 404B may be photodetectors, photoresistors, or the like. Although detection device 400 in this example has two light sources and two detectors, it is envisioned that the detection device

400 may include any suitable number of light sources and detectors suitably arranged and operable for measuring turbidity.

With continuing reference to FIG. 7A, during operation light sources 402A, 402B may simultaneously or at different times generate and direct light towards a sample contained within a cuvette or a solution holder 406. As shown in the figure, the light sources 402A, 402B are arranged about the sample 406 and oriented to direct light into the cuvette 406 and onto the sample contained therein. This example shows a particular arrangement of light sources 402A, 402B about the perimeter of the cuvette 406, but it should be understood that the light sources and detectors may be alternatively arranged and spaced apart from each other for directing light towards a sample.

For the purpose of clarity, FIG. 7A depicts only light source 402A directing light into the cuvette 406. Particularly, broken line arrow 408 represents the general direction of the path of light generated by light source 402A and transmitted through the sample. The transmitted light 408 is received by the detector 404B positioned at a side of the cuvette 406 that opposes the position of light source 402A. Scattered light 410 may be received by detector 404A at a 90°.

FIG. 7B depicts the detection device 400 with light 412 being generated by light source 402A and directed towards the sample. Transmitted light may be received by the detector 404A positioned at a side of the cuvette 406 that opposes the position of light source 402B. Scattered light 410 may be received by detector 404B at a 90°.

Although not shown in FIGS. 7A and 7B, the detectors 404A, 404B may be operably connected to a suitable computing device having hardware, software, firmware, or a combination thereof for implementing functionality disclosed herein for analyzing the turbidity of the sample. An example equation that may be applied by the computing device for analyzing turbidity of the sample 110 follows:

$$T = Cal_{slope} * \sqrt{\frac{Active1 * Active2}{Reference1 * Reference2}} - Cal_0$$

where T represents turbidity in NTU, $Cal_{slope}$ represents a calibration coefficient, $Cal_0$ represents a calibration coefficient, Active1 represents 90 degree detector current (light source 402A ON, light source 402B OFF), Active2 represents 90 degree detector current (light source 402A OFF, light source 402B ON), Reference1 represents transmitted detector current (light source 402A ON, light source 402B OFF), and Reference2 represents transmitted detector current (light source 402A OFF, light source 402B ON). A representation of the determined turbidity may be displayed or otherwise presented on a user interface controlled by the computing device.

Figure 8:
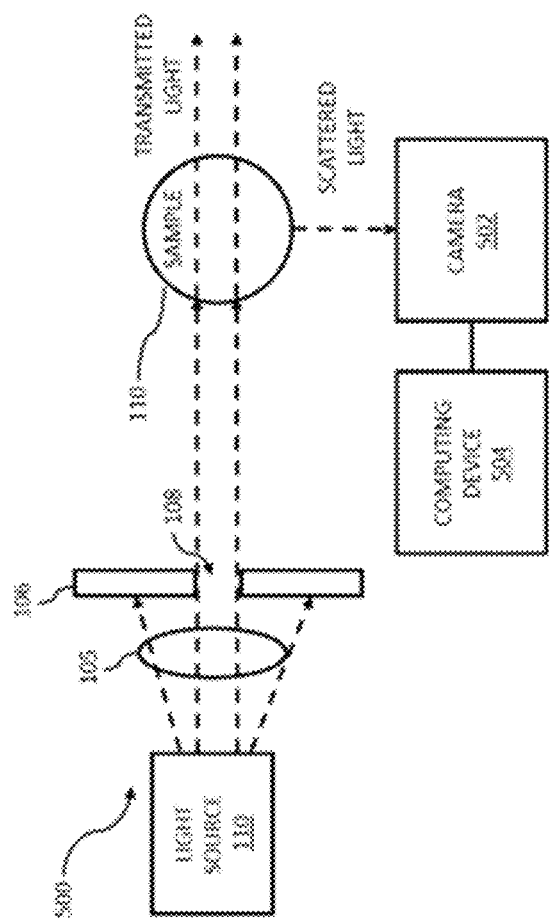
FIG. 8 is a schematic of an embodiment of a detection device 500 including a camera 502 for measuring turbidity.

In an embodiment, a camera or other image capture device may be used for detecting scattered and/or transmitted light. The camera may be used in place of a photodetector or photoresistor for example FIG. 8 is a schematic of an embodiment of a detection device 500, or turbidimeter, including a camera 502 for measuring turbidity. The layout of the detection device 500 shown in FIG. 8 is similar to the detection device 100 shown in FIG. 4 except that the detector 112 is replaced with the camera 502 for receipt of the scattered light. The camera 502 is configured to capture an image or video based on the received scattered light. Further, the camera 502 may digitize the capture image and/or video and communicate to a computing device 504 an electrical signal representative of the capture image and/or video. The computing device 504 has hardware, software, firmware, or a combination thereof for implementing functionality disclosed herein for analyzing the turbidity of the sample 110.

Figure 9A:
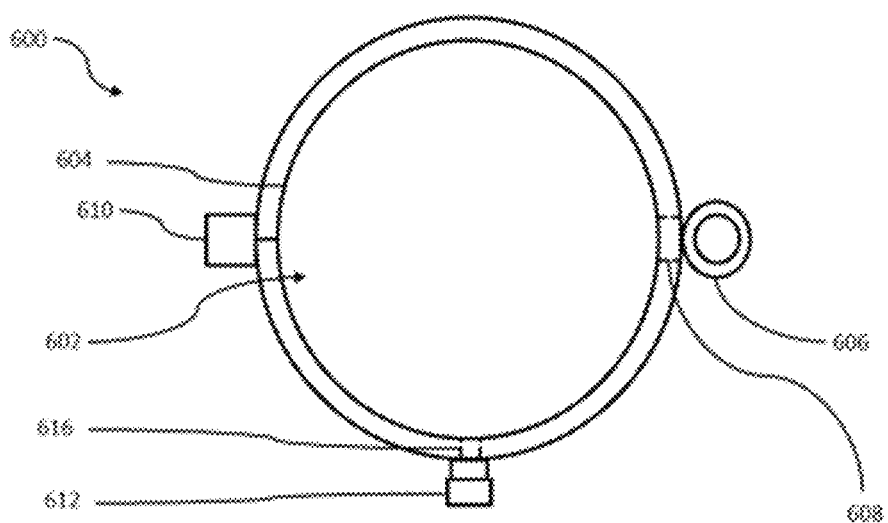
FIG. 9A is a top view of an embodiment of a cuvette holder, generally designated 600, having a cylindrical shape in an embodiment.
Figure 9B:
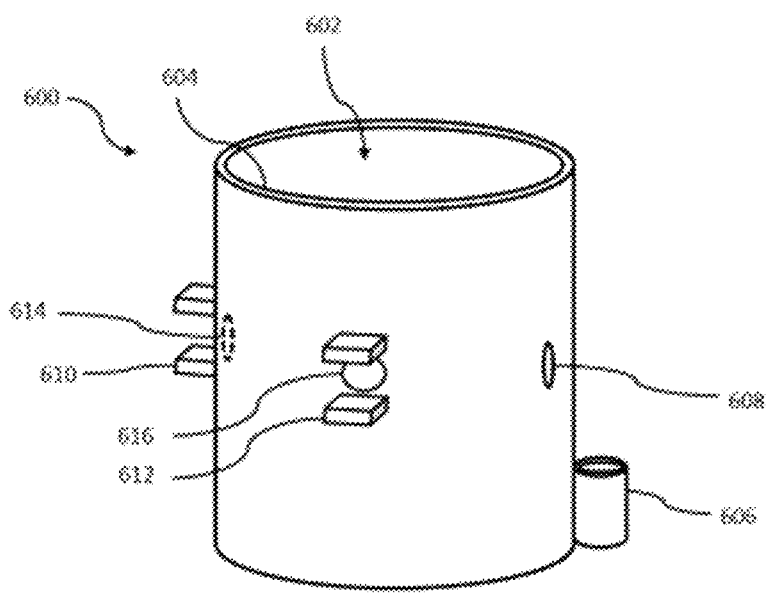
FIG. 9B is a top perspective view of an embodiment of a cuvette holder, generally designated 600, having a cylindrical shape in an embodiment.

In another embodiment, an embodiment of a cuvette holder is described, wherein an example cuvette is cylindrical or substantially cylindrical in shape, but is not limited to same. An interior of a cuvette holder may be similarly shaped and sized for receiving a cylindrically shaped cuvette. FIGS. 9A and 9B are a top view and a top perspective view, respectively, of a cuvette holder, generally designated 600, having a cylindrical shape in an embodiment. Referring to FIGS. 9A and 9B, the cuvette holder 600 defines an interior space 602 and opening 604 for receiving a cuvette therein. The received cuvette is cylindrically shaped and sized for insertion through the opening 604 and into the interior space 602 for holding by the cuvette holder 600 during operation of a detection device in accordance with an embodiment of the present disclosure.

With continuing reference to FIGS. 9A and 9B, the cuvette holder 600 may include at least one light source holder 606 for holding a light source in a position to direct its light inside a held cuvette. It should be appreciated that a source of radiation, i.e., a light, is inserted in the light source holder 606, such that the radiation enters the aperture 608. Light from the light source may enter the cuvette holder though an aperture 608. Further, the cuvette holder 600 may include multiple detector holders 610 and 612 for holding detectors that can receive transmitted light and scattered light, respectively. The detector holders 610 and 612 may be associated with apertures 614 and 616, respectively, for passage of light from the interior space 602 to their respective detectors. Although not shown in FIGS. 9A and 9B, additional holders and apertures are contemplated for the collection of backscattered light and forward scattered light.

Figure 9C:
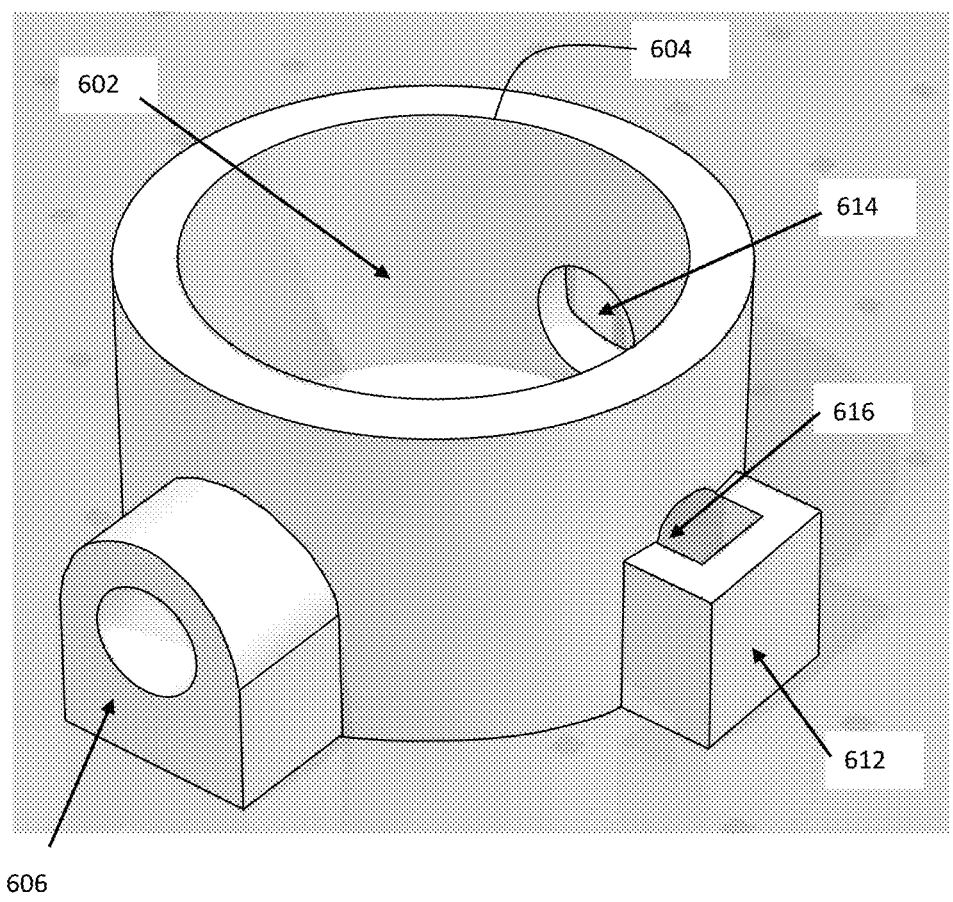
FIG. 9C is a top perspective view of another embodiment of a cuvette holder having a cylindrical shape in an embodiment.

Another embodiment of the cuvette holder is illustrated in FIG. 9C. As will be appreciated by the person skilled in the art, the cuvette holders of 9A-9C are not intended to limit the size, shape or arrangement of the cuvette holder. They are provided for illustrative purposes only.

The cuvette holder preferably is an enclosure for the cuvette, i.e., chemical sensor, to keep light out while simultaneously reducing electrical noise from the at least one detector during measurements. The cuvette holder preferentially permits only light provided by the at least one light source to pass through and be received by the at least one detector. Advantageously, the cuvette holder such as that shown in FIGS. 9A-9C can be integrated, having holders (a) for the positioning of at least one light source at the at least one light source aperture, and (b) for the positioning of at least one detector at the corresponding at least one detector aperture. Although not shown, the integrated cuvette holder can further comprise at least one of (a) a holder for at least one temperature sensor, if present, (b) a holder for a humidity detector, if present, (c) a "lock and key" fit, (d) a holder for the agitator, if present, and (e) a plug that is insertable in a corresponding socket for energy introduction to at least the light source(s) and the detectors(s). Although not shown, the cuvette holder can be designed to assist with the removal of the cuvette from said holder, for example, a small hole in the bottom of the integrated cuvette holder through which a pointed article can be placed to push the cuvette out of the cuvette holder.

Advantageously, the detection device and the integrated cuvette holder can be designed to permit the insertion of the integrated cuvette holder in a corresponding socket or slot on or in the detection device, wherein the integrated cuvette holder as a whole can be removed from the detection device. The removal of the integrated cuvette holder from the detection device permits the user to (a) easily replace the cuvette with a cuvette comprising fresh chemistries, (b) replace the at least one light source, (c) replace the at least one detector, (d) replace any of the optional equipment including, but not limited to, a temperature sensor, a humidity detector, and an agitator, (e) replace the membrane on the cuvette, or (f) replace the entire cuvette holder. The corresponding socket or slot can have all of the required energy connections, e.g., a plug with a corresponding socket, or alternatively, the cuvette holder can comprise at least one wire with a plug that is inserted into a corresponding socket in the detection device. It is also contemplated that the cuvette holder can comprise the actual source of energy, for example, the cuvette holder can comprise a holder for the placement of a battery, wherein the battery powers only the devices associated with the integrated cuvette holder or the battery powers the integrated cuvette holder and other parts of the modular unit. Accordingly, the removal of the integrated cuvette holder from the detection device permits the user to (g) easily replace the battery, when present, as well.

Accordingly, in a fourth aspect, a detection device is described herein, wherein the detection device comprises:
a cuvette holder, wherein the cuvette holder has a shape and size that accommodates a cuvette, wherein the cuvette comprises a sample under test;
at least one light source configured to generate a light beam and to direct the light beam to the sample under test;
at least one detector configured to receive light that is one of transmitted through the sample or scattered by the sample, and configured to generate an output representative of one of the transmitted or scattered light; and
a computing device configured to receive the output from the at least one detector and to determine a characteristic of the sample based on the received output.

In a fifth aspect, an integrated cuvette holder is described, wherein the cuvette holder has a shape and size that accommodates a cuvette, said integrated cuvette holder comprising: (a) a holder for at least one light source and a corresponding aperture to direct light emanating from each light source to an interior space of the cuvette holder;
(b) a holder for at least one detector and a corresponding aperture for the passage of light from the interior space of the cuvette holder to each detector;
(c) optionally a holder for a temperature sensor;
(d) optionally a holder for a humidity detector;
(e) optionally a holder for an agitator,
wherein the integrated cuvette holder is an enclosure that minimizes light in the interior space while simultaneously reducing electrical noise in the interior space from the at least one detector.

In an embodiment, a detection device or turbidimeter includes the modular unit or housing for containing its electronic components and cuvette holder. The modular unit may include an opening leading to a cuvette holder for holding a cuvette. The modular unit may be box-shaped or have any other suitable shape and be made of any suitable material, such as plastic, polymeric material that can prevent interference from light and outside vibration. The detection device may be operable in conditions between about −25° C. and about 90° C., depending on robustness of the battery used, as readily understood by the person skilled in the art. The modular unit may hold a suitable power source such as a battery (e.g., a AA battery or a lithium ion battery), or be operable to receive electrical power from an outside power source. It is noted that the modular unit may include one or more apertures (e.g., slits) to improve air circulation within the modular unit to cool electronic components located therein. In another example, a fan may be utilized for cooling the electronic components. In still another embodiment, the power source is used to power an agitator that is provided to agitate the mixture in the cuvette.

Figure 10:
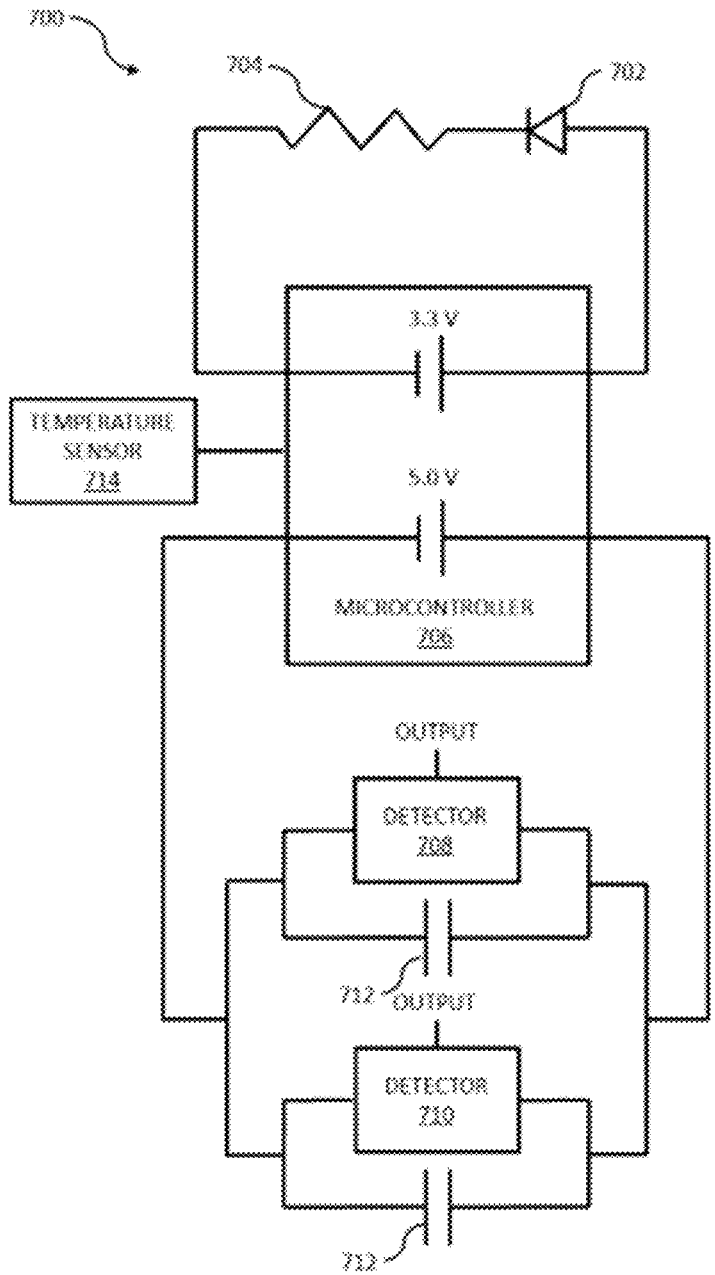
FIG. 10 is a circuit diagram of an embodiment of a portion of a detection device 700.

FIG. 10 is a circuit diagram of an embodiment of a portion of a detection device of the system described herein. This example detection device 700 may comprise components implemented in the configuration shown in FIG. 6. Referring to FIG. 10, the detection device 700 includes an LED 702 configured to generate and to direct a light beam towards a sample under analysis being held by a cuvette or other sample holder. A resistor 704 may be utilized in series with the LED 702 to restrict current flow for controlling over current of the LED 702.

The LED 702 and the resistor 704 are also connected in series with a microcontroller 706. The microcontroller 706 may include suitable hardware, software, firmware, or combination thereof for controlling the LED 702 to generate light in accordance with embodiments of the present disclosure. In an example, the microcontroller 706 may be an ESP 32 microcontroller that applies 3.3 V across the LED 702 and resistor 704 to control the LED 702 to generate light for application to the sample. Further, in this example, the LED 702 outputs red light at 633 nm, and the resistor 704 has a resistance of 220 ohms. It is noted that, in an example, the LED 702 may correspond to the light source 102 shown in FIG. 6. Further, it should be appreciated by the person skilled in the art that the wavelength of the light source and the resistance of the photoresistor detector is not limited to this example, but instead are readily determined by the person skilled in the art depending on the perishable product to be detected, the nature of the chemical or physical sensor, and other environmental conditions.

The detection device 700 also includes detectors 708 and 710 for receiving scattered light and transmitted light, respectively, in accordance with embodiments of the present disclosure. For example, detectors 708 and 710 may correspond to detectors 112 and 352, respectively, shown in FIG. 6. Each detector 708 and 710 is connected in parallel with a respective capacitor 712. The microcontroller 706 may supply 5.0 V of power across the detectors 708 and 710 and their capacitor 712. The capacitors 712 may be 100 nF or any have any other suitable capacitance. The detectors 708 and 710 may be photodetectors, photoresistors, or the like. Outputs of the detectors 708 and 710 may be operably connected to the microcontroller 706 for receipt of electrical signals representative of the detected scattered and transmitted light. The microcontroller 706 may use the received scattered and transmitted light data for analysis of the sample in accordance with embodiments disclosed herein. In an example of use of an ESP 32 microcontroller, the outputs of the detectors 708 and 710 may be connected to pins GPIO21 and GPIO34, respectively, of the microcontroller.

During example operation of the detection device 700 for sample analysis, the LED 702 is controlled to emit light, which is directed towards a cuvette. The light may be scattered and/or transmitted. Detectors 708 and 710 receive scattered light irradiance and transmitted light irradiance, respectively, and convert the light irradiance to frequency, which may be electrical square waves output to the microcontroller 706. The microcontroller 706 receives the signals that are representative of the scattered light irradiance and transmitted light irradiance. Subsequently, the microcontroller 706 may convert the signals indicative of frequency to turbidity in accordance with embodiments of the present disclosure. The microcontroller 706 may communicate the determined turbidity to another computing device.

To convert frequency to turbidity, the following example equations may be utilized by the microcontroller 706. For example, the microcontroller 706 may convert frequency to light irradiance by use of the following equation:

$$I = a*f$$

where I represents light irradiance, a represents sensor coefficient*1, and f represents frequency.

Further, the microcontroller 706 may convert light irradiance to turbidity by use of the following equation:

$$T = \frac{I_{90}}{d_t * I_t + d_{90} * I_{90}}$$

where T represents turbidity in NTU, d* represents calibration coefficient of each angle, and I* represents light intensity of each angle.

The microcontroller 706 may be suitably connected to a display device or another computing device configured to receive and present to a user sample analysis data or raw data obtained during testing of a sample. For example, the microcontroller 706 may be operably connected to a desktop computer, laptop computer, smartphone, or tablet computer for display of the analysis or raw data, or further analysis of the data. The microcontroller 706 may be hardwired to the computing device for data communication or may be wirelessly connected to the computing device (e.g., WI-FI® wireless communication).

In another embodiment, the detection device 700 shown in FIG. 10 may optionally include a temperature sensor 714 and/or a humidity detector (not shown) operably connected to the microcontroller 706. The temperature sensor 714 may detect ambient temperature and convert the temperature to voltage or another signal output to the microcontroller 706 for indicating the detected temperature. The microcontroller 706 may use the temperature data to correct or adjust turbidity. The following equation may be used by the microcontroller 706 for converting voltage to temperature:

$$d = b*v$$

where d represents temperature in degrees, b represents sensor coefficient*2, and v represents voltage. The determined temperature may be used to adjust the turbidity measurement.

Figure 11:
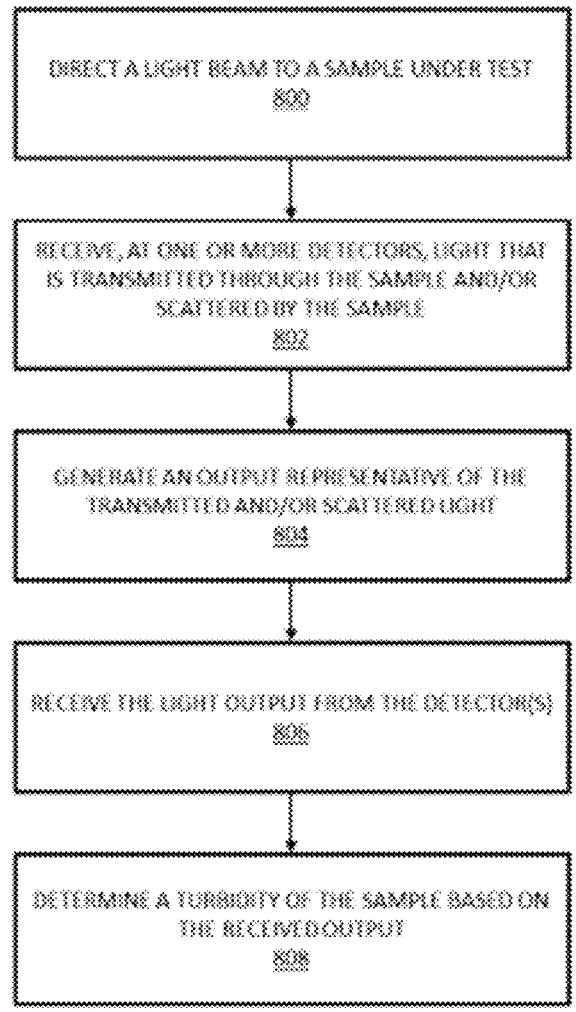
FIG. 11 is a flow chart of an example method for determining turbidity of a sample under test in accordance with an embodiment of the present disclosure.

FIG. 11 is a flow chart of an example method for determining turbidity of a sample under test in accordance with an embodiment of the present disclosure. The method is described by example as being implemented by the detection device 350 shown in FIG. 6, although it should be understood that the method may alternatively be implemented by any other suitable detection device measuring other chemical or physical changes associated with microbial growth or microbial decay, and include for example, the detection of at least one of carbon dioxide, oxygen, ethylene, hydrogen sulfide, ammonia, volatile and non-volatile amines, total volatile nitrogen, volatile acids and bases, non-volatile acids and bases, slime formation, *E. coli, Salmonella, Listeria monocytogenes*, or combination thereof.

Referring to FIG. 11, the method includes directing 800 a light beam to a sample under test. For example, the light source 102 of the detection device 350 shown in FIG. 6 may generate and direct a light beam to the sample 110. A microcontroller or other suitable computing device may control the light source to generate the light. An example microcontroller for controlling the light source 102 includes, but is not limited to, the microcontroller 706 shown in FIG. 10.

The method of FIG. 11 includes receiving 802, at at least one detector, light that is one of transmitted through the sample or scattered by the sample. Further, the method of FIG. 11 includes generating 804, at the at least one detector, an output representative of the one of the transmitted or scattered light. Continuing the aforementioned example, detectors 112 and 352 shown in FIG. 6 may receive scattered light and transmitted light, respectively, from the sample 110. The detectors 112 and 352 may convert the intensity of the received light to electrical signals and may output the electrical signals to the microcontroller or computing device.

The method of FIG. 11 includes receiving 806 the output from the at least one detector. Continuing the aforementioned example, the microcontroller 706 shown in FIG. 10 may receive electrical signals representative of the intensities of the scattered and transmitted light. Data indicative of the intensities of the light communicated by the electrical signals may be suitably stored on memory of the microcontroller 706.

The method of FIG. 11 includes determining 808 turbidity of the sample based on the received output. Continuing the aforementioned example, the microcontroller 706 of FIG. 10 may determine turbidity of the sample based on the data representative of the intensities of the scattered and transmitted light. The microcontroller 706 may implement a suitable algorithm to determine the turbidity based on the light intensities. In an example, the microcontroller 706 may use only the scattered light intensity for determining the turbidity. In another example, the microcontroller 706 may use the scattered light intensity and the transmitted light intensity for determining the turbidity. In yet another example, the microcontroller 707 may use multiple different scattered light intensities (e.g., back scattered light intensity, forward scattered light intensity, 90° angle scattered intensity, the like, or a combination thereof) and the transmitted light intensity for determining the turbidity.

Figure 12:
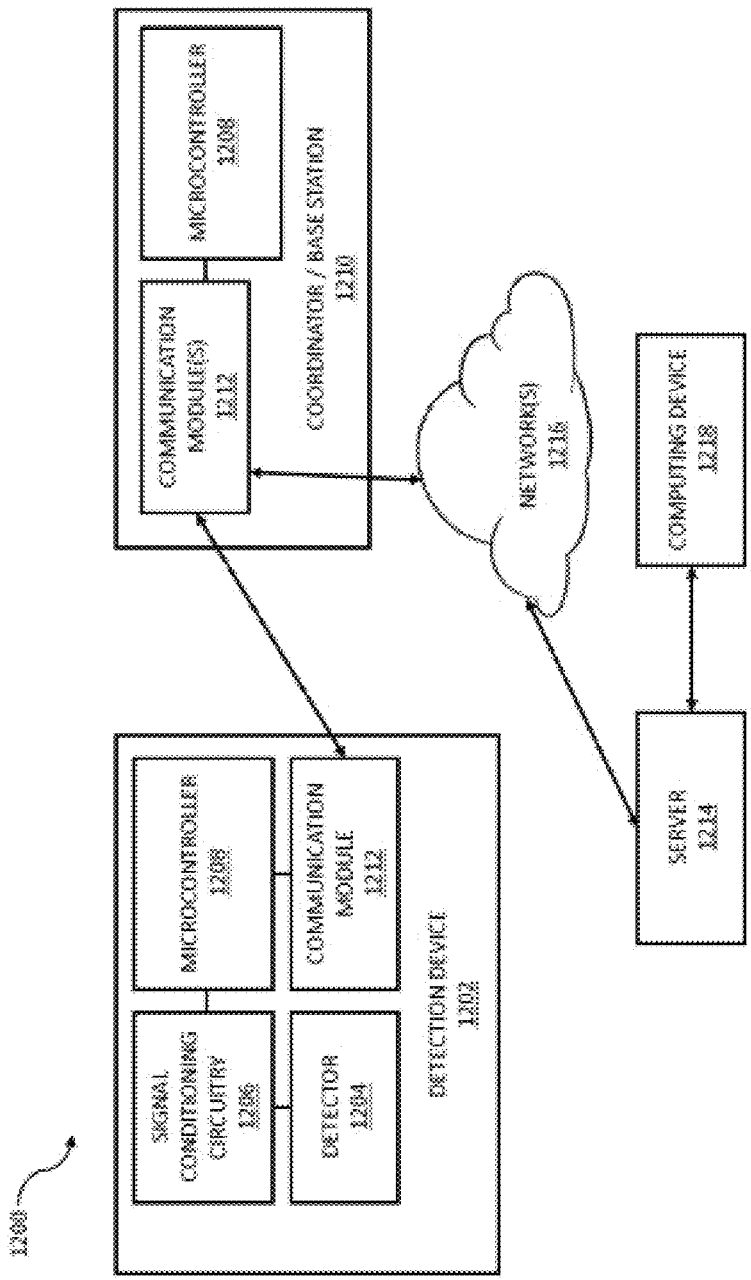
FIG. 12 illustrates a schematic of the electronics portion of a detection system 1200 in accordance with an embodiment.

FIG. 12 illustrates a schematic of the electronics portion of a detection system 1200 in accordance with an embodiment. This detection system may utilize or incorporate one or more example components and processes disclosed herein. For example, the system 1200 includes a detection device 1202 that can include the functionality and components of detection devices described herein for detecting turbidity of a sample under test. The detection device 1202 may include a detector 1204 that is configured to receive light transmitted and/or scattered by the sample. Further, the detector 1204 can generate an electrical signal representative of the transmitted and/or scattered light. The electrical signal may be output to signal conditioning circuitry 1206 for filtering, amplifying, the like, or a combination thereof. The conditioned electrical signal may be output by the signal conditioning circuitry 1206 to a microcontroller 1208. The microcontroller 1208 is configured to receive the conditioned electrical signal and to determine the turbidity of the sample based on the conditioned electrical signal in accordance with embodiments disclosed herein.

With continuing reference to FIG. 12, the detection device 1202 is configured to communicate the determined turbidity to another computing device, such as a coordinator/base station 1210. Particularly, the detection device 1202 and the base station 1210 each include a communication module 1212 that is configured to exchange data with each other. For example, the communication modules 1212 may implement a suitable wireless communication technology such as, but not limited to IEEE 802.15.4 wireless communication technology, for communication with each other. In an example, the communication modules 1212 may be Xbee radios or the like. The communication module 1212 may receive the turbidity data from the microcontroller 1208 and may communicate the turbidity data to the communication module 1212 of the base station 1210. The base station 1210 may include a microcontroller 1212 that receives the turbidity data from the communication module 1212 of the base station 1210. Further, the base station 1210 may include multiple communication modules 1212, including a communication module configured to communicate the turbidity data to a server 1214 via one or more networks 1216. In turn, the server 1214 may communicate the turbidity data to another computing device (e.g. a smartphone, tablet computer, or the like) 1218 either via network(s) 1216 or directly.

Figure 13:
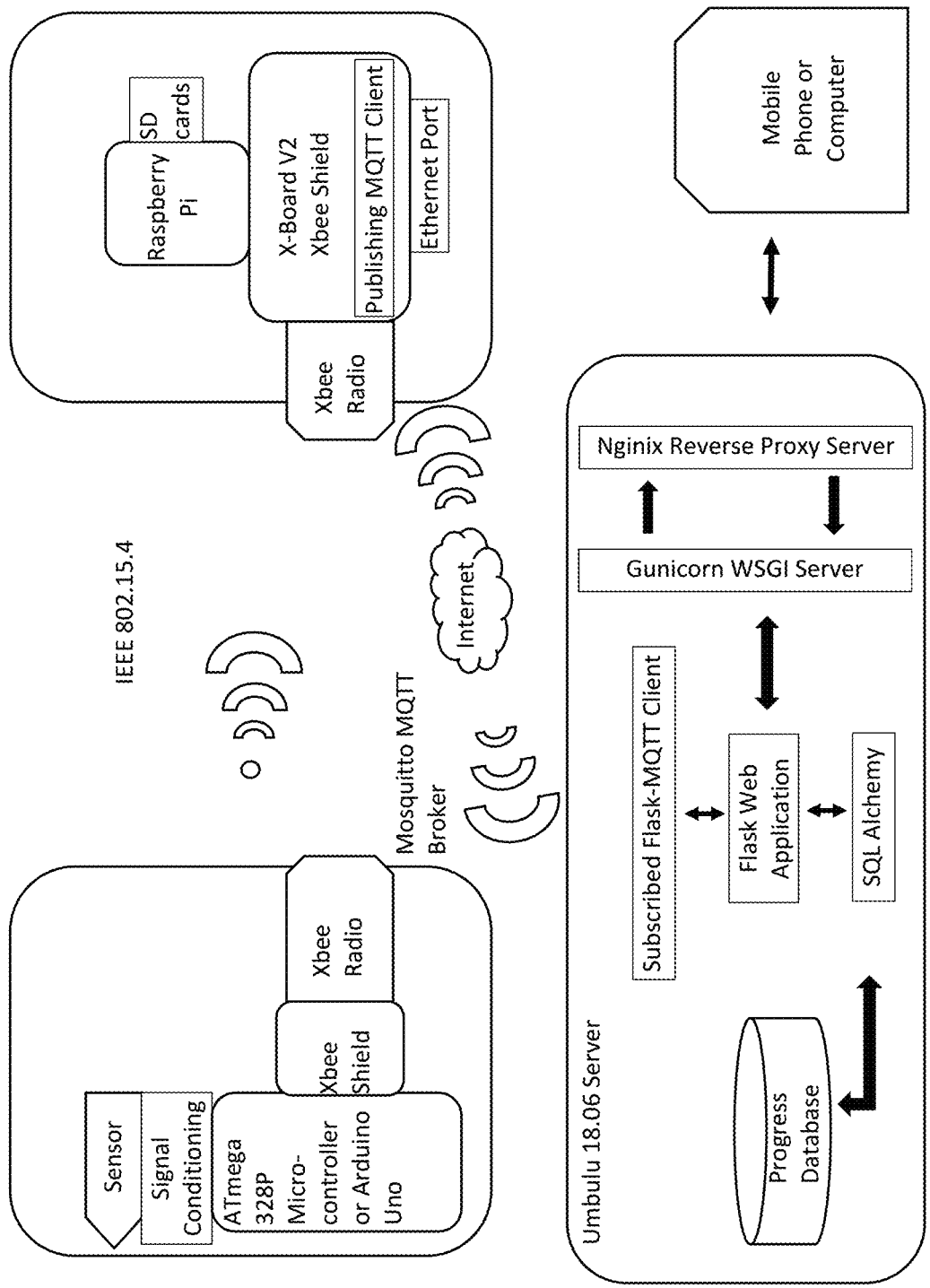
FIG. 13 illustrates a specific example of the schematic of FIG. 12.

FIG. 13 illustrates a specific example of the schematic of FIG. 12.

In a sixth aspect, a detection system is described, said detection system comprising:
a detection device comprising:
a cuvette holder, wherein the cuvette holder has a shape and size that accommodates a cuvette, wherein the cuvette comprises a sample under test;
at least one light source configured to generate a light beam and to direct the light beam to the sample under test;
at least one detector configured to receive light that is one of transmitted through the sample or scattered by the sample, and configured to generate an output representative of one of the transmitted or scattered light;
a first computing device configured to receive the output from the at least one detector and to determine a characteristic of the sample based on the received output; and
a communication module configured to communicate the determined characteristic of the sample; and
a second computing device configured to receive the determined characteristic of the sample.

Intelligent Bandages

Another source of microbial growth is wounds on patients as the wounds progress towards healing. As defined herein, a "patient" includes human beings, mammals, amphibians, birds, sealife, and plants. Wounds include, but are not limited to, cuts, scrapes, or any other format that exposes the interior of the living matter and has to go through a natural process of healing.

Similar to the system described hereinabove, an intelligent bandage comprising the sensor and the detection device (or the modular unit) is positioned in close proximity to the wound. The sensor can comprise the same components described hereinabove, wherein only USDA approved chemicals are used, e.g., calcium hydroxide. Alternatively, food grade indicators can be used. When using the microbial growth detection system as an intelligent bandage, an analog display such as a color change response is preferred so as to quickly and easily ascertain if the bandage needs to be replaced. The analog display can be provided on the output display. In another embodiment, the intelligent bandage system is configured to provide an analog display on the surface of the bandage. This could be done by including the digital output device and the output display in the modular unit per se.

Notably, because the intelligent bandage comprises the sensor and detection device (or the modular unit) described herein, the intelligent bandage can be fabricated to be relatively small and inexpensive to make. Moreover, with the advent of 3-D printing, the intelligent bandage comprising a modular unit can be fabricated to specifically fit over the specific wound of the patient.

Method of Using

In a seventh aspect, a method for detecting microbial growth on or in a perishable product, is described, said method comprising:
(I) positioning a chemical sensor and a detection device in a location proximate to the perishable product;
(II) measuring at least one characteristic of microbial growth on or in the perishable product using the chemical sensor in cooperation with the detection device;
(III) converting at least one characteristic of the chemical sensor to digitized data;
(IV) transmitting the digitized data to a digital output device;
(V) algorithmically analyzing the digitized data to determine the extent of microbial growth on or in the perishable product; and
(VI) displaying the extent of microbial growth on an output display to inform a user if the perishable product should be disposed of or sterilized.

It should be understood by the person skilled in the art that if the amount of bacterial growth on or in the perishable product is above a prescribed threshold that the perishable product should be discarded or sterilized (if possible). The "location" of positioning of the sensor and detection device can be in a chamber as defined herein or can be for example, positioned over or near a wound. In a preferred embodiment, the method of detecting microbial growth on or in a perishable product uses any one of the systems described in the first, second, third or sixth aspects described herein. The algorithmic analysis is performed using a computing device. The detection device can digitize the relative light opacity (or color) of the solution in the cuvette to frequency or electromotive force (i.e., an electrical signal). In one embodiment, the detection device in the seventh aspect is the one described herein in the fourth aspect. In one embodiment, the cuvette is present in a cuvette holder as for example described herein in the fifth aspect.

In another embodiment of the seventh aspect, a method for detecting microbial growth on or in a perishable product, is described, said method comprising:
(I) positioning a carbon dioxide sensor and a detection device in a location proximate to the perishable product;
(II) measuring turbidity in the $CO_2$ sensor using the sensor in cooperation with the detection device;
(III) converting the turbidity to digitized data;
(IV) transmitting the digitized data to a digital output device;
(V) algorithmically analyzing the digitized data to determine the extent of microbial growth on or in the perishable product; and
(VI) displaying the extent of microbial growth on an output display to inform a user if the perishable product should be disposed of or sterilized.

It should be understood by the person skilled in the art that if the amount of bacterial growth on or in the perishable product is above a prescribed threshold that the perishable product should be discarded or sterilized (if possible). The "location" of positioning of the sensor and detection device can be in a chamber as defined herein or can be for example, positioned over or near a wound. In a preferred embodiment, the method of detecting microbial growth on or in a perishable product uses any one of the systems described in the first, second, third or sixth aspects described herein. The algorithmic analysis is performed using a computing device. The detection device can digitize the relative light opacity (or color) of the solution in the cuvette to frequency or electromotive force (i.e., an electrical signal). In one embodiment, the detection device in the seventh aspect is the one described herein in the fourth aspect. In one embodiment, the cuvette is present in a cuvette holder as for example described herein in the fifth aspect.

In still another embodiment of the seventh aspect, a method for detecting microbial growth on or in a perishable product, is described, said method comprising:
(I) positioning a modular unit in a location proximate to the perishable product, wherein the modular unit comprises a carbon dioxide sensor and a detection device;
(II) measuring turbidity in the $CO_2$ sensor using the sensor in cooperation with the detection device;
(III) converting the turbidity to digitized data;
(IV) transmitting the digitized data to a digital output device;
(V) algorithmically analyzing the digitized data to determine the extent of microbial growth on or in the perishable product; and
(V) displaying the extent of microbial growth on a device that permits the user to conclude if the perishable product can still be used or consumed.

It should be understood by the person skilled in the art that if the amount of bacterial growth on or in the perishable product is above a prescribed threshold that the perishable product should be discarded or sterilized (if possible). The "location" of positioning of the sensor and detection device can be in a chamber as defined herein or can be for example, positioned over or near a wound. In a preferred embodiment, the method of detecting microbial growth on or in a perishable product uses any one of the systems described in the first, second, third or sixth aspects described herein. The algorithmic analysis is performed using a computing device. The detection device can digitize the relative light opacity (or color) of the solution in the cuvette to frequency or electromotive force (i.e., an electrical signal). In one embodiment, the detection device in the seventh aspect is the one described herein in the fourth aspect. In one embodiment, the cuvette is present in a cuvette holder as for example described herein in the fifth aspect.

Other Aspects

As introduced hereinabove, the chemical species in the chemical sensor may be prepared by the user but in many scenarios, a manufacturer will prepare and provide the chemical species to the user. For example, the modular unit comprises a chemical sensor comprising a cuvette holder for the positioning of a cuvette. The cuvette comprises at least one species that reacts with the byproduct of microbial growth. If the species undergoes an irreversible reaction, the contents of the cuvette cannot be reused. Accordingly, the modular unit comprises a cuvette holder wherein cuvettes comprising fresh chemistries (i.e., reactants for the chemical reaction) can be inserted therein and withdrawn at the completion of the chemical reaction, for reuse of the modular unit. Used cuvettes can be sent back to the manufacturer and recycled for reuse. Towards that end, the cuvette and cuvette holder described herein can have a physical "lock and key" aspect that permits only the insertion of certain cuvettes in the certain cuvette holders. Alternatively, the cuvette comprises an independent identifier including, but not limited to, an RFID tag, microchip, or QR code, wherein the identifier on the cuvette is scanned and the system only works if the identifier is approved for the modular unit.

Another aspect of the microbial growth detection system and method of using same is the use of RFID tags/infrastructure to send an alert when perishable products are approaching their expiry date of the maximum permitted amount of microbial growth, thereby establishing communication between consumers and their refrigerators. RFID systems consists of a tag and a scanner and are well known in the art as being able to use the electromagnetic energy to power themselves and send data to the network or cloud-based system. The range of the scanner is up to a few meters. Up to 300 tags/second can be read.

Embodiments of the MAD system and method of using same advantageously provide, for example, sensors, digital output devices, computing devices and computer-readable program products, and related methods to track perishable products from the date of harvest, packaging or shipment, to the date the consumer or restaurant obtains the perishable product, and every stop in between. The technology disclosed herein can utilize a blockchain-based transaction platform to access and track multiple transactions among various parties involved in the growth, manufacture, production, shipment, and storage of the perishable products and its subsequent delivery for consumption to a restaurant or individual household. Any trusted individual or company can access the blockchain-based transaction platform to verify the information associated with any of the records associated with a particular perishable product.

As discussed herein, the sensors of the apparatus include a modular unit that measures various desired parameters, for example the concentration of $CO_2$ in a chamber. The modular unit integrates with the digital output devices which can be configured using the computer-readable program products to directly send the data to the blockchain-based platform.

Determining whether a perishable product is otherwise safe for administration or consumption is one of the main purposes of the MAD systems and method of using same. Quality control and quality assurance of the perishable product is vital. A system comprising a blockchain platform may use a pass or fail system based on a standardization of $CO_2$ levels for the specific perishable product.

Moreover, certain embodiments of the disclosure involve the systems, computer-readable program product, and related computer-implemented methods to obtain information from the users and generate user reports, according to embodiments of the present disclosure as discussed above. These embodiments can be implemented using one or more computing devices, one or more servers, one or more databases, one or more cloud computing configurations, and one or more communications networks.

Certain embodiments of the disclosure include a system for collecting a plurality of information related to a perishable product and maintaining a database. The plurality of information can also include information from inventory tracking software. The information collected can be used to ensure that the MAD apparatus and method of using same is continually optimized to maximize quality control and quality assurance. Any databases discussed herein may include relational, hierarchical, graphical, blockchain, object-oriented structure and/or any other database configurations. The databases may be organized in any suitable manner, for example, as data tables and/or lookup tables. Each record may be a single file, a series of files, a linked series of data fields or any other data structure.

Because the MAD system is able to track the modular units and the perishable products being monitored by said modular units, the source, location, and destination of the perishable products can be efficiently and effectively identified in the event that the perishable products must be recalled when they, or the same lot, are deemed no longer safe for use or consumption.

It should be appreciated that the MAD system contemplates uses in association with web services, utility computing, pervasive and individualized computing, security and identity solutions, autonomic computing, cloud computing, commodity computing, mobility and wireless solutions, open source, biometrics, grid computing and/or mesh computing.

Because of the inclusion of computing devices, all data and information can be stored, including information relating to perishable products that were used or disposed of subsequent to a reading.

Advantageously, the microbial growth detection system and method of using same generates information that can allow a user to make informed decisions about food consumption based on the extent of microbial growth, i.e., the freshness indicator. This invention can have economies of scale and can be utilized by everyone in the food supply value chain including, but not limited to, farmers, processors, distributors, storage facilities, as well as in retail stores, food service operations, and households.

It is expected that this invention can be implemented in a wide variety of ways. It will be appreciated that procedures described above are carried out repetitively as necessary. To facilitate understanding, aspects of the invention are described in terms of actions that can be performed by, for example, elements of a programmable computing device or by specialized circuits, by program instructions executed by one or more processors, or by a combination of both.

Computing Devices

The functional units described in this specification have been labeled as computing devices. A computing device may be implemented in programmable hardware devices such as processors, digital signal processors, central processing units, field programmable gate arrays, programmable array logic, programmable logic devices, cloud processing systems, or the like. The computing devices may also be implemented in software for execution by various types of processors. An identified device may include executable code and may, for instance, comprise one or more physical or logical blocks of computer instructions, which may, for instance, be organized as an object, procedure, function, or other construct. Nevertheless, the executable of an identified device need not be physically located together but may comprise disparate instructions stored in different locations which, when joined logically together, comprise the computing device and achieve the stated purpose of the computing device. In another example, a computing device may be a server or other computer located within one environment and communicatively connected to other computing devices (e.g., POS equipment or computers) for managing processes. In another example, a computing device may be a mobile computing device such as, for example, but not limited to, a smart phone, a cell phone, a pager, a personal digital assistant (PDA), a mobile computer with a smart phone client, or the like. In another example, a computing device may be any type of wearable computer, such as a computer with a head-mounted display (HMD), or a smart watch or some other wearable smart device. A computing device can also include any type of conventional computer, for example, a laptop computer or a tablet computer. A typical mobile computing device is a wireless data access-enabled device (e.g., an iPHONE® smart phone, a BLACKBERRY® smart phone, a *NEXUS* ONE™ smart phone, an iPAD® device, smart watch, or the like) that is capable of sending and receiving data in a wireless manner using protocols like the Internet Protocol, or IP, and the wireless application protocol, or WAP. This allows users to access information via wireless devices, such as smart watches, smart phones, mobile phones, pagers, two-way radios, communicators, and the like. Wireless data access is supported by many wireless networks, including, but not limited to, Bluetooth, Near Field Communication, CDPD, CDMA, GSM, PDC, PHS, TDMA, FLEX, ReFLEX, iDEN, TETRA, DECT, DataTAC, Mobitex, EDGE and other 2G, 3G, 4G, 5G, and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone or smart watch that operates over GPRS (General Packet Radio Services), which is a data technology for GSM networks or operates over Near Field Communication e.g., Bluetooth. In addition to a conventional voice communication, a given mobile device can communicate with another such device via many different types of message transfer techniques, including Bluetooth, Near Field Communication, SMS (short message service), enhanced SMS (EMS), multi-media message (MMS), email WAP, paging, or other known or later-developed wireless data formats. Although the system and process described herein are implemented on smart devices, they may similarly be implemented on any suitable computing device, such as a computer.

An executable code of a computing device may be a single instruction, or many instructions, and may even be distributed over several different code segments, among different applications, and across several memory devices. Similarly, operational data may be identified and illustrated herein within the computing device and may be embodied in any suitable form and organized within any suitable type of data structure. The operational data may be collected as a single data set or may be distributed over different locations including over different storage devices, and may exist, at least partially, as electronic signals on a system or network.

The device or system for performing one or more operations on a memory of a computing device may be software, hardware, firmware, or combination of these. The device or the system is further intended to include or otherwise cover all software or computer programs capable of performing the various heretofore-disclosed determinations, calculations, or the like for the disclosed purposes. For example, exemplary embodiments are intended to cover all software or computer programs capable of enabling processors to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed below.

As used herein, the term "memory" is generally a storage device of a computing device. Examples include, but are not limited to, read-only memory (ROM) and random access memory (RAM).

Computer readable program instructions can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The computer readable program instructions can be written in exemplary programming languages that execute from memory on the device or from a hosted server, such as BASIC, COBOL, C, C++, Java, Pascal, or scripting languages such as JavaScript, Python, Ruby, PHP, Perl, or other suitable programming languages. The computer readable program instructions may execute entirely on the user's computing device, partly on the user's computing device, as a stand-alone software package, partly on the user's computing device and partly on a remote computing device or entirely on the remote computing device or server. In the latter scenario, the remote computing device may be connected to the user's computing device through any type of network, including a local area network (LAN) or a wide area network (WAN), or the connection may be made to an external computing device (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

As referred to herein, a user interface is generally a system by which users interact with a computing device. A user interface can include an input for allowing users to manipulate a computing device, and can include an output display for allowing the system to present information and/or data, indicate the effects of the user's manipulation, etc. An example of a user interface on a computing device (e.g., a mobile device) includes a graphical user interface (GUI) that allows users to interact with programs in more ways than typing. A GUI typically can offer display objects, and visual indicators, as opposed to text-based interfaces, typed command labels or text navigation to represent information and actions available to a user. For example, an interface can be a display window or display object, which is selectable by a user of a mobile device for interaction. A user interface can include an input for allowing users to manipulate a computing device, and can include an output for allowing the computing device to present information and/or data, indicate the effects of the user's manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. The display object can be displayed on a display screen of a computing device and can be selected by and interacted with by a user using the user interface. In an example, the display of the computing device can be a touch screen, which can display the display icon. The user can depress the area of the display screen where the display icon is displayed for selecting the display icon. In another example, the user can use any other suitable user interface of a computing device, such as a keypad, to select the display icon or display object. For example, the user can use a track ball or arrow keys for moving a cursor to highlight and select the display object.

The output display can be a display screen of a mobile device or other computing device and can be selected by and interacted with by a user using an interface. In an example, the display of the mobile device can be a touch screen, which can display the display icon. The user can depress the area of the display screen at which the display icon is displayed for selecting the display icon. In another example, the user can use any other suitable interface of a computing device, such as a keypad, to select the display icon or display object. For example, the user can use a track ball or times program instructions thereon for causing a processor to carry out aspects of the present disclosure.

As referred to herein, a computer network may be any group of computing systems, devices, or equipment that are linked together. Examples include, but are not limited to, local area networks (LANs) and wide area networks (WANs). A network may be categorized based on its design model, topology, or architecture. In an example, a network may be characterized as having a hierarchical internetworking model, which divides the network into three layers: access layer, distribution layer, and core layer. The access layer focuses on connecting client nodes, such as workstations to the network. The distribution layer manages routing, filtering, and quality-of-server (QoS) policies. The core layer can provide high-speed, highly redundant forwarding services to move packets between distribution layer devices in different regions of the network. The core layer typically includes multiple routers and switches.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network, or Near Field Communication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions. These computer readable program instructions may be provided to a processor of a computing device, special purpose computing device, or other programmable data processing apparatus to produce a machine, such that the instructions, which execute via the processor of the computing device or other programmable data processing apparatus, create means for implementing the functions/acts specified in the flowchart and/or block diagram block or blocks. These computer readable program instructions may also be stored in a computer readable storage medium that can direct a computing device, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computing device, other programmable data processing apparatus, or other device to cause a series of operational steps to be performed on the computing device, other programmable apparatus or other device to produce a computer implemented process, such that the instructions which execute on the computing device, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the invention may be embodied in many different forms, not all of which are described above, and all such forms are contemplated to be within the scope of the invention. It is emphasized that the terms "comprises" and "comprising," when used in this application, specify the presence of stated features, steps, or components and do not preclude the presence or addition of one or more other features, steps, components, or groups thereof.

The particular embodiments described above are merely illustrative and should not be considered restrictive in any way. The scope of the invention is determined by the following claims, and all variations and equivalents that fall within the range of the claims are intended to be embraced therein.

What is claimed is:

1. A detection system comprising:
   a detection device comprising:
      a cuvette holder, wherein the cuvette holder has a shape and size that accommodates a cuvette, wherein the cuvette comprises a sample under test;
      at least one light source configured to generate a light beam and to direct the light beam to the sample under test;
      at least one detector configured to receive light that is one of transmitted through the sample or scattered by the sample, and configured to generate an output representative of one of the transmitted or scattered light;
      a first computing device configured to receive the output from the at least one detector and to determine a characteristic of the sample based on the received output; and
      a communication module configured to communicate the determined characteristic of the sample; and
   a second computing device configured to receive the determined characteristic of the sample,
   wherein the cuvette comprises at least one wall comprising a gas-permeable microporous membrane capable of byproduct diffusion therethrough and at least one wall that is optically transparent in the wavelengths employed by the light source.

2. The detection system of claim 1, wherein the communication module is configured to wirelessly communicate the determined characteristic of the sample to the second computing device.

3. The detection system of claim 1, further comprising a third computing device, wherein the second computing device is configured to communicate the determined characteristic of the sample to the third computing device.

4. The detection system of claim 1, wherein liquids and solids cannot penetrate the gas-permeable microporous membrane.

5. The detection system of claim 1, wherein the at least one light source comprises a light emitting diode (LED).

6. The detection system of claim 1, wherein the first computing device is configured to determine relative light opacity based on intensity of the transmitted light, scattered light, or both.

7. The detection system of claim 1, wherein the detection device further comprises at least one of:

(a) an agitator selected from the group consisting of a mixer, a magnetic stirrer coupled with a spinning magnet, a propeller, a vibrator, a sonicator, and combinations thereof;
(b) a temperature sensor;
(c) a humidity detector; or
(d) any combination of (a)-(c).

8. The detection system of claim 1, wherein the at least one detector comprises one of a photodetector and a photoresistor.

9. The detection system of claim 8, wherein the at least one detector is configured to receive light scattered by the sample at 90° relative to the at least one light source, backscattered, forward scattered, or any combination thereof.

10. The detection system of claim 1, wherein the cuvette holder is integrated and comprises a holder for the at least one light source and a holder for the at least one detector.

11. The detection system of claim 10, wherein the integrated cuvette holder further comprises (a) an aperture to direct light emanating from each light source to the sample, and (b) an aperture for light transmitted through the sample or scattered by the sample to each detector.

12. The detection system of claim 10, wherein the integrated cuvette holder further comprises at least one of a holder for a temperature sensor, a holder for a humidity detector, and a holder for an agitator.

13. The detection system of claim 10, wherein the integrated cuvette holder further comprises (a) an aperture to direct light emanating from each light source to the sample, (b) an aperture for light transmitted through the sample or scattered by the sample to each detector, and (c) optionally at least one of a holder for a temperature sensor, a holder for a humidity detector, a holder for an agitator, or a holder for an energy source.

14. The detection system of claim 10, wherein the integrated cuvette holder is an enclosure that minimizes light in the interior space while simultaneously reducing electrical noise in the interior space from the at least one detector.

15. The detection system of claim 1, further comprising a chemical sensor.

16. The detection system of claim 15, wherein the chemical sensor detects a byproduct of microbial growth, wherein said byproduct is selected from the group consisting of carbon dioxide, oxygen, ethylene, hydrogen sulfide, ammonia, volatile amines, total volatile nitrogen, and volatile acids and bases.

17. The detection system of claim 1, wherein the characteristic is selected from the group consisting of Nephelometric Turbidity Units (NTU), milkiness, relative light opacity, turbidity, opalescence, redox potential change, light intensity change, and color change.

18. The detection system of claim 15, wherein the chemical sensor is a $CO_2$ sensor and the at least one characteristic is relative light opacity, wherein the detection device can digitize the relative light opacity of the $CO_2$ sensor to a frequency or an electromotive force.

19. A method for detecting microbial growth on or in a perishable product in real time, said method comprising:
(I) positioning a chemical sensor and the detection system of claim 1 in a location proximate to the perishable product;
(II) measuring at least one characteristic of microbial growth on or in the perishable product using the chemical sensor in cooperation with the detection device;
(III) converting at least one characteristic of microbial growth to digitized data;
(IV) transmitting the digitized data to a digital output device;
(V) algorithmically analyzing the digitized data to determine the extent of microbial growth on or in the perishable product; and
(VI) displaying the extent of microbial growth on an output display to inform a user if the perishable product should be disposed of or sterilized.

20. The method of claim 19, wherein digital output device correlates the digitized data from the detection device to the extent of microbial growth in or on the perishable product.

* * * * *